United States Patent
Asogawa et al.

(10) Patent No.: US 8,628,732 B2
(45) Date of Patent: Jan. 14, 2014

(54) IMMOBILIZING DEVICE AND IMMOBILIZATION METHOD USING THE IMMOBILIZATION DEVICE

(75) Inventors: Minoru Asogawa, Tokyo (JP); Hayataro Kochi, Tokyo (JP)

(73) Assignee: NEC Corporation, Tokyo (JP)

( * ) Notice: Subject to any disclaimer, the term of this patent is extended or adjusted under 35 U.S.C. 154(b) by 145 days.

(21) Appl. No.: 13/119,246

(22) PCT Filed: Oct. 19, 2009

(86) PCT No.: PCT/JP2009/005459
§ 371 (c)(1), (2), (4) Date: Mar. 16, 2011

(87) PCT Pub. No.: WO2010/044282
PCT Pub. Date: Apr. 22, 2010

(65) Prior Publication Data
US 2011/0171089 A1    Jul. 14, 2011

(30) Foreign Application Priority Data

Oct. 17, 2008    (JP) ................................. 2008-268905

(51) Int. Cl.
*G01N 15/06* (2006.01)

(52) U.S. Cl.
USPC ............. 422/561; 422/50; 422/401; 422/402; 422/63; 422/68.1; 422/502; 422/503; 422/560; 422/565; 422/566

(58) Field of Classification Search
USPC .............. 422/50, 401, 402, 63, 68.1, 81, 502, 422/503, 560, 565, 566
See application file for complete search history.

(56) References Cited

U.S. PATENT DOCUMENTS

| 5,551,487 A * | 9/1996 | Gordon et al. ..................... 141/1 |
| 6,446,326 B1 * | 9/2002 | Mastromatteo et al. ... 29/603.04 |
| 2010/0008748 A1 * | 1/2010 | Godot et al. ............... 414/217.1 |

FOREIGN PATENT DOCUMENTS

| JP | 2002228671 A | 8/2002 |
| JP | 2003156490 A | 5/2003 |
| JP | 2003187933 A | 7/2003 |

OTHER PUBLICATIONS

International Search Report for PCT/JP2009/005459 mailed Jan. 12, 2010.

* cited by examiner

*Primary Examiner* — Brian J Sines

(57) ABSTRACT

Provided is an immobilization device for fitting a connecting member of a chip and a connecting member of a cover together, where a spatial clearance between the chip and cover is small. The immobilization device includes a substrate (102), a cover means (101) including a fitting means to fit with a chip (103) placed on the substrate (102), a rotating arm means (201) rotatably joined to a first joining means (301) of the substrate (102) and to a second joining means (302) of the cover means (101), and a parallel maintaining means (203) for fitting the fitting means and the chip (103) together with the fitting means and the chip (103) maintained in substantially parallel by the first joining means (301) or the second joining means (302) moving along a chip surface or a plane parallel to the chip surface. The fitting means rotates freely against the chip (103).

19 Claims, 15 Drawing Sheets

IMMOBILIZING DEVICE AND IMMOBILIZATION METHOD USING THE IMMOBILIZATION DEVICE

TECHNICAL FIELD

The present invention relates to an immobilizing device and an immobilization method using the immobilization device.

BACKGROUND ART

μ-TAS (Total Analysis system) is a chemical analysis system used in the medical or environmental measurement field, and analysis of a micro sample is performed using the same. In the μ-TAS, a micro pump, valve, sensor and so on are integrated.

Some μ-TAS are produced by forming a channel or a vessel on a surface of a glass or plastic substrate. Such a substrate is referred to hereinafter as a chip. When performing sample analysis using the chip, it is necessary to feed a sample or reagent to the channel or the vessel of the chip. Further, in order to perform processing such as stirring or mixing of a liquid sample or a solid sample fed to the channel or the vessel of the chip, it is necessary to externally apply a pressure or the like to the chip.

Such an operation on the chip is performed as follows using a tube attachment. One end of a tube is connected to a feeding device for feeding a sample, reagent, pressure or the like to the chip. The other end of the tube is connected to a fitting unit (e.g. socket). The chip is equipped with a connecting member (e.g. plug) which is connectable with the socket. When the socket is placed on the cover, the socket and the plug can be connected by connecting the cover to the chip. When the socket is connected to the plug, a sample or the like is fed from the feeding device to the chip through the tube.

When performing the above-described operation on the chip, it is necessary to make a certain spacing between the chip and the cover. For example, when attaching the cover to the chip, the chip is first mounted in a given position. To execute this operation, a spatial clearance for operating the chip is needed between the chip and the cover. For example, when a person mounts the chip in a given position, a space allowing a person's hand to freely move is required between the chip and the cover. Further, when mounting the chip in a given position using a mounting device, a space for using the mounting device is required between the chip and the cover. Furthermore, the visibility of the chip needs to be ensured in order to visually check the way the chip is mounted. On this account also, a spatial clearance is needed between the chip and the cover.

Patent Literature 1 discloses a sample solution spotting device that makes spotting of a sample probe into wells of the substrate in a substantially uniform amount. In this device, in order to suck in samples held in wells of a container called a microtiter plate, the tips of suction needles are inserted into the wells of the container. The device has a mechanism which makes a holder holding the suction needles move up and down. The device disclosed in Patent Literature 1 operates as follows. Note that the holder is referred to as a cover unit 101, a member which is a part of the device and on which the chip is mounted is referred to as a substrate 102, and the container is referred to as a chip 103.

First, the cover unit 101 is moved up in order to mount the chip 103 on the substrate 102 (FIG. 19B). The cover unit 101 moves upward in a direction perpendicular to the chip 103 with use of a mechanism which moves the cover unit 101 in the direction perpendicular to the chip 103. In this manner, operability and visibility of the chip can be ensured, and the chip 103 can be thereby mounted on the substrate 101.

After the chip 103 is mounted on the substrate 102, the cover unit 101 moves downward in the direction perpendicular to the chip 103 and is connected to the chip 103 (FIG. 19A). Then, the tips of the suction needles are brought down perpendicularly to the container and reach samples contained in the wells.

CITATION LIST

Patent Literature

[Patent Literature 1]
Japanese Unexamined Patent Application Publication No. 2002-228671

SUMMARY OF INVENTION

Technical Problem

However, it is not preferable to leave a large spatial clearance between the chip and the cover as in the device disclosed in Patent Literature 1. This is because an increase in a spacing between the chip and the cover leads to an increase in size and complexity of the device. Further, when connecting a tube to a socket of the cover unit, a long tube is required (FIG. 19B). The long tube makes handling complicated. Furthermore, because the tube is elastic, it expands when a pressure is applied inside the tube. Thus, the long tube makes it difficult to control the pressure inside the tube. In addition, in the case of feeding a reagent, the long tube causes an increase in the volume (dead volume) of the reagent accumulated inside the tube.

Therefore, it is preferable that a spacing between the chip and the cover is as small as possible.

An object of the present invention to provide an immobilizing device for fitting a fitting unit to fit with a chip and the chip together, in which a spatial clearance between the chip and the fitting unit is small.

Solution to Problem

A device according to the present invention includes a substrate, a cover means comprising a fitting means to fit with a chip placed on the substrate, a rotating arm means rotatably joined to a first joining means of the substrate and further joined to a second joining means of the cover means, and a parallel maintaining means for making the fitting means to fit with the chip with the fitting means and the chip maintained in substantially parallel relation by the first joining means or the second joining means moving along a chip surface or a plane parallel to the chip surface. The fitting means rotates freely with respect to the chip.

Advantageous Effects of Invention

According to the present invention, it is possible to provide an immobilizing device for fitting a chip and a fitting unit together, in which a spatial clearance between the chip and the fitting unit is small.

DESCRIPTION OF EMBODIMENTS

Figure 1:
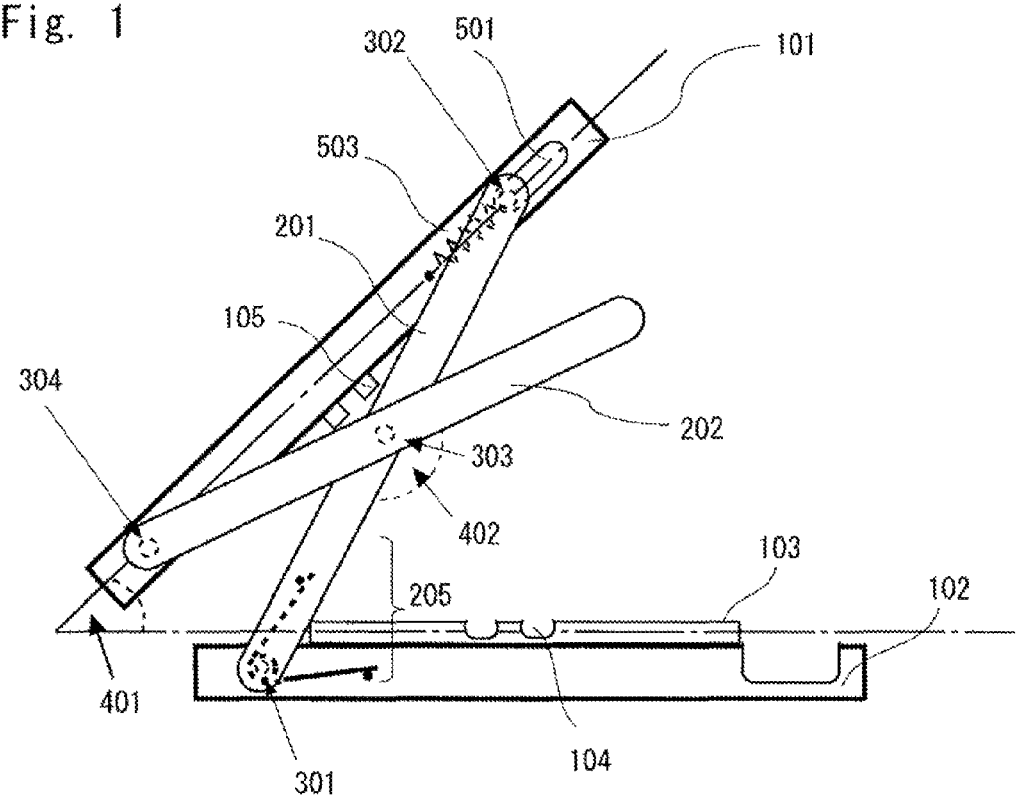
FIG. 1 is a view showing an immobilizing device according to the present invention.

Exemplary embodiments of the present invention will be described hereinafter with reference to the drawings. In the figures, the same elements are denoted by the same reference symbols. Further, redundant explanation is omitted.

It should be noted that the present invention is not restricted to the exemplary embodiments described below but is susceptible of numerous changes and modifications within the scope of its technical idea.

First Exemplary Embodiment

A first exemplary embodiment describes an immobilization device which includes a substrate, a cover unit that includes a fitting unit to fit with a chip placed on the substrate, a rotating arm unit that is rotatably joined to a first joint of the substrate and is further joined to a second joint of the cover unit, and a parallel maintaining unit that makes the fitting unit to fit with the chip with the fitting unit and the chip maintained in substantially parallel relation by the first joint or the second joint moving along a chip surface or a plane parallel to the chip surface, in which the fitting unit rotates freely with respect to the substrate.

In the substrate, the rotating arm unit is rotatably joined to the first joint of the substrate. The rotating arm unit is also joined to the second joint of the cover unit. The cover unit includes the fitting unit. The fitting unit fits with the chip placed on the substrate. The fitting unit is freely rotatable with respect to the substrate.

Further, the first joint or the second joint can move along a plane parallel to the chip surface. In this structure, the fitting unit and the chip can fit with each other with the fitting unit and the chip maintained in substantially parallel relation.

The way the present device operates when making the chip placed on the substrate and the fitting unit fit with each other is described hereinbelow. The operation of the device involves a first operation that makes the fitting unit and the chip parallel to each other from the position that the cover unit rotates about the end of the cover unit as a rotation center, and a second operation that makes the fitting unit to fit with the chip with the fitting unit and the chip maintained in parallel positions. Specifically, the first operation changes the state from the state of FIG. 1 to the state of FIG. 2. The second operation changes the state from the state of FIG. 2 to the state of FIG. 3. Although the operation is described using FIGS. 1 to 3 for the sake of simplicity, the exemplary embodiment is not limited to the structures of FIGS. 1 to 3.

Note that, in this specification, the directions of up, down, left and right which are used in the description using the drawings are defined as follows. The direction from the fitting unit to the chip in a direction perpendicular to a chip surface or a plane parallel to the chip surface is referred to as a downward direction. The direction from the chip to the fitting unit in the direction perpendicular to the chip surface or the plane parallel to the chip surface is referred to as an upward direction. The direction toward the right when viewing the drawing in the direction parallel to the chip surface or the plane parallel to the chip surface is referred to as a rightward direction. The direction toward the left when viewing the drawing in the direction parallel to the chip surface or the plane parallel to the chip surface is referred to as a leftward direction.

First, prior to the operation of the present device, the chip 103 is placed in a given position of the substrate 102 (FIG. 1). The given position is a position in which the cover unit and the fitting unit fit with each other when the fitting unit in parallel relation to the chip is brought into contact with the chip with use of the device.

As shown in FIG. 1, the cover unit 101 that has the fitting unit is in a rotating position about its end as a rotation center with respect to the chip. This is because the cover unit 101 is freely rotatable with respect to the chip 103. In FIG. 1, the fitting unit and the cover unit 101 are integrated together. The cover unit 101 is rotatably joined to the first joint of the substrate 102. This structure enables the fitting unit to rotate with respect to the chip.

By the rotation of the fitting unit with respect to the chip, a sufficient spatial clearance can be obtained between the chip and the fitting unit. Therefore, the chip 103 can be easily placed on the substrate 102 in this device.

Figure 2:
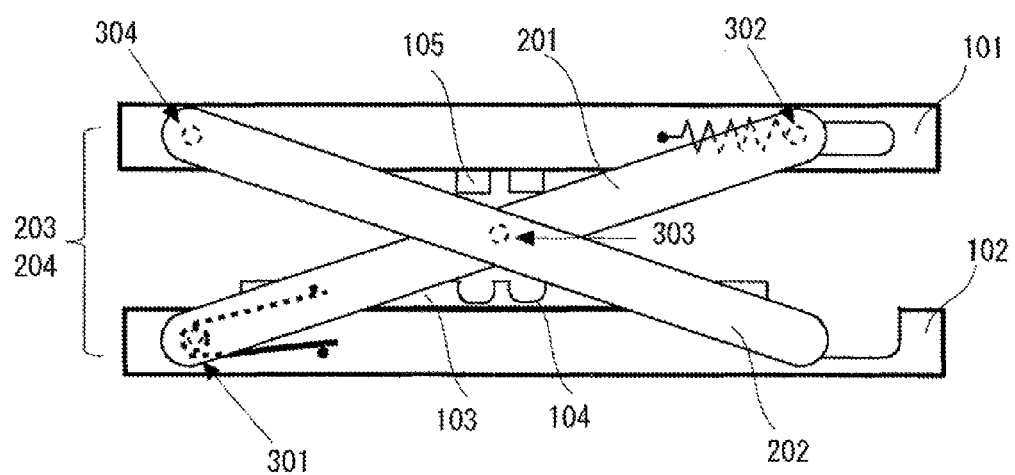
FIG. 2 is a view showing the immobilizing device according to the present invention.

Next, the first operation is executed. Specifically, the fitting unit is made to rotate with respect to the chip, so that the fitting unit and the chip become parallel to each other. In the example of FIG. 1, a force in the direction from the cover unit 101 to the chip 103 is applied to the cover unit 101. In other words, a force in the downward direction from the cover unit 101 is applied to the cover unit 101. Then, the cover unit 101 and the chip 103 are brought into substantially parallel positions as shown in FIG. 2.

Next, the second operation is executed. Specifically, the fitting unit and the chip are made to fit with each other with the fitting unit and the chip maintained in substantially parallel relation. When the fitting unit and the chip are made closer, the first joint or the second joint moves along a chip surface or along a plane parallel to the chip surface in this device. In the example of FIG. 2, when a downward force is applied to the cover unit 101, the cover unit 101 moves downward. Further, concurrently with the downward movement of the cover unit 101, the second joint moves along a plane parallel to the chip surface. The second joint moves rightward. As a result of the concurrent execution of such movement, the fitting unit and the chip fit with each other, remaining in parallel relation to each other.

In this manner, the fitting unit and the chip can fit with each other with the fitting unit and the chip maintained in substantially parallel positions in the present device. Further, by rotating the cover unit 101 when operating the chip, a space to ensure operability and visibility of the chip can be obtained between the cover unit and the chip. Further, the space between the cover unit and the chip can be suppressed to the minimum necessary, thus allowing downsizing and simplification of the immobilizing device.

The present device allows the connecting member of the fitting unit and the connecting member of the chip to fit with each other with the chip and the cover unit maintained in substantially parallel relation by use of a parallel maintaining mechanism. Importance of the parallel maintaining mechanism is described hereinbelow.

Figure 20:
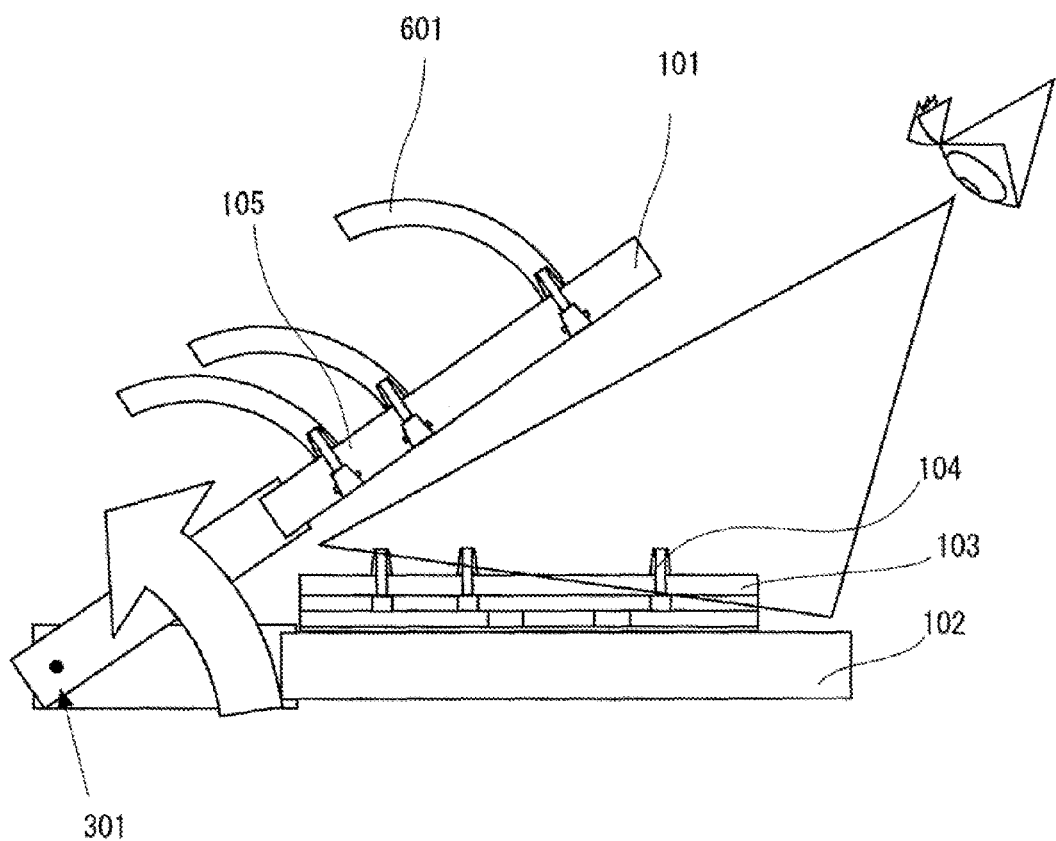
FIG. 20 is a view showing an immobilizing device not including a parallel maintaining mechanism and a spacing maintaining mechanism.

A structure of a device which does not include a parallel maintaining mechanism is as shown in FIG. 20, for example. In the device shown in FIG. 20, one end of the cover unit 101 having the fitting unit is rotatably connected to the substrate 102. In this structure, the cover unit 101 can rotate to be tilted. As a result, a space can be created between the chip 103 and the cover unit 101. The space ensures operability and visibility for the chip 103.

However, in the device shown in FIG. 20, the fitting unit and the chip fail to accurately fit with each other. This is because the fitting unit and the chip come into contact in the state where the fitting unit and the chip are not parallel to each other. Issues which occur when connecting the connecting member of the fitting unit and the connecting member of the chip in the case of using the device of FIG. 20 are described hereinafter with reference to FIGS. 21A to 21C.

Figure 21A:
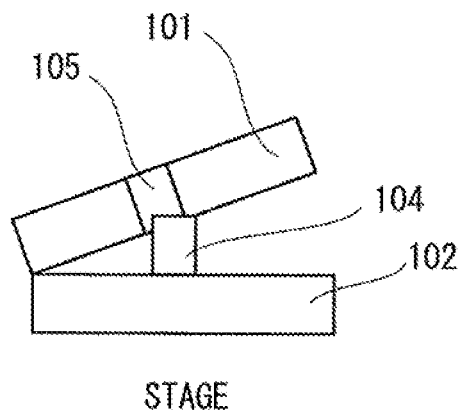
FIG. 21A is a view when connecting a connecting member of a chip and a connecting member of a fitting unit with use of an immobilizing device not including a parallel maintaining mechanism and a spacing maintaining mechanism.

For example, a connecting member 105 of the fitting unit and a connecting member 104 of the chip collide with each other and cannot fit with each other as shown in FIG. 21A.

Figure 21B:
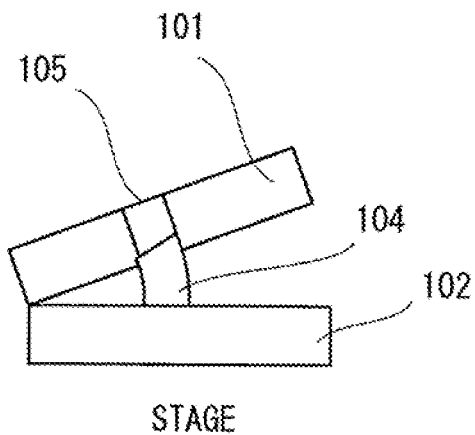
FIG. 21B is a view when connecting a connecting member of a chip and a connecting member of a fitting unit with use of an immobilizing device not including a parallel maintaining mechanism and a spacing maintaining mechanism.

Alternatively, either connecting member is bent as shown in FIG. 21B. Such a state causes breakage to the connecting member and is not preferable.

Figure 21C:
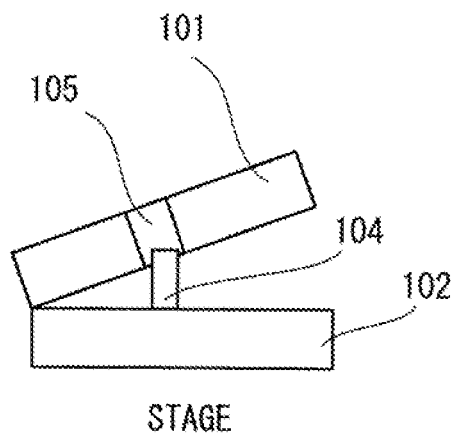
FIG. 21C is a view when connecting a connecting member of a chip and a connecting member of a fitting unit with use of an immobilizing device not including a parallel maintaining mechanism and a spacing maintaining mechanism.

Alternatively, the plug-shaped connecting member 104 of the chip is smaller than the socket-shaped connecting member 105 of the fitting unit as shown in FIG. 21C. In this state, the plug and the socket do not match, causing leakage of a sample or pressure.

Alternatively, measures may be taken to avoid the above-described issues. Specifically, utilizing that the connecting member of the fitting unit moves along a circular trajectory about the first joint 301, the connecting member may be formed in advance to a shape corresponding to the circular orbit. However, such a shape is more complex than a normal shape of the connecting member, thus not preferable.

As described above, the device without inclusion of the parallel maintaining mechanism has a problem that, although a space can be created between the fitting unit and the chip, the connecting member of the fitting unit and the connecting member of the chip cannot accurately fit with each other. On the other hand, with inclusion of the parallel maintaining mechanism, the present device enables a space to be created between the fitting unit and the chip and also enables the connecting member of the fitting unit and the connecting member of the chip to accurately fit with each other.

The above description regarding the operation of the present device is given on the operation until making the fitting unit to fit with the chip after mounting the chip on the substrate. Hereinafter, the operation of detaching the fitting unit and the chip after fitting them together is described.

The operation after that involves a third operation that detaches the fitting unit and the chip with the fitting unit and the chip maintained in parallel to each other, and a fourth operation that rotates the fitting unit with respect to the chip and makes a spatial clearance between the fitting unit and the chip.

The third operation that detaches the fitting unit from the chip is as follows. An upward force is applied to the cover unit 101 in the state of FIG. 3. Then, the cover unit 101 is detached from the chip 103 and moves upward. Further, concurrently with the upward movement of the cover unit 101, the second joint moves leftward along a plane parallel to the chip surface. As a result of the concurrent execution of such movement, the fitting unit and the chip, which have been fit together, are detached, remaining in parallel relation to each other (FIG. 2).

Then, the fitting unit is made to rotate with respect to the chip so as to create a spatial clearance between the fitting unit and the chip. In FIG. 1, the cover unit 101 having the fitting unit may rotate with respect to the chip 103.

By the above operation, the fitting unit and the chip which have been fit together can be detached. Further, by the above operation, a spatial clearance can be obtained between the fitting unit and the chip. Because the fitting unit moves upward in parallel with the chip, breakage of the connecting member of the fitting unit and the connecting member of the chip can be prevented.

As the parallel maintaining mechanism, Scott-Russell mechanism may be used. The Scott-Russell mechanism indicates a mechanism that converts a certain linear motion into a linear motion in a direction substantially orthogonal to input. In the case of the present invention, a part of a force acting on the fitting unit and in a direction perpendicular to the chip surface is converted into a force in a direction parallel to the chip surface by the Scott-Russell mechanism. Then, the first joint or the second joint moves along the chip surface or a plane parallel to the chip surface. Note that the chip surface indicates a surface of the chip to which the fitting unit is fixed.

As described above, according to the present device, it is possible to provide a space for ensuring operability and visibility of the chip between the fitting unit and the chip as well as reducing a spatial clearance between the fitting unit and the chip. Further, it is possible to fit the fitting unit and the chip together with the fitting unit and the chip maintained in substantially parallel relation to each other.

Second Exemplary Embodiment

Figure 3:
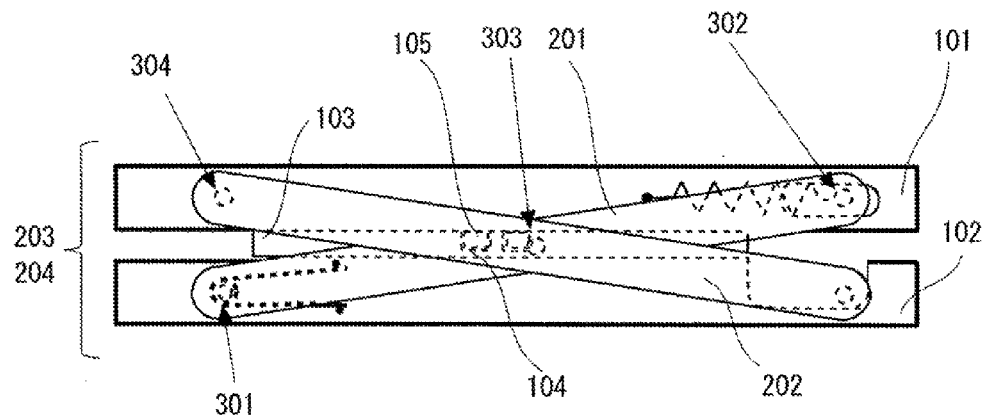
FIG. 3 is a view showing the immobilizing device according to the present invention.

In a second exemplary embodiment, an immobilization device according to the second exemplary embodiment is described with reference to FIGS. 1, 2 and 3.

The device according to the second exemplary embodiment includes the substrate 102. The chip 103 is placed on the substrate 102. A rotating arm unit 201 is rotatably joined to the first joint 301 of the substrate 102. The cover unit 101 is joined to the second joint 302 of the rotating arm unit 201. A third joint 303 is located between the first joint 301 and the second joint 302 of the rotating arm unit 201. A supporting arm unit 202 is rotatably joined to the third joint 303. Further, the supporting arm unit 202 is joined to a fourth joint 304 of the cover unit 101. The cover unit 101 includes the fitting unit to fit with the chip.

Further, the supporting arm unit 202 is rotatably joined to the fourth joint 304.

The rotating arm unit 201, the cover unit 101 and the supporting arm unit 202 of the device operate in conjunction with one another.

Further, the device includes a parallel maintaining mechanism 203, a spacing control mechanism 204, and a rotation (tilt) control mechanism 205. The parallel maintaining mechanism 203 makes the connecting member 105 of the fitting unit and the connecting member 104 of the chip to fit together with the chip 103 placed on the substrate and the cover unit 101 maintained in substantially parallel relation. The spacing control mechanism 204 controls a spacing between the cover unit 101 and the chip 103. The rotation control mechanism 205 controls an angle 401 between the cover unit 101 and the chip 103.

Further, in this device, the cover unit 101 has a cover slide part 501 for implementing the parallel maintaining mechanism 203. The second joint 302 of the rotating arm unit 201 slides on the cover slide part 501.

Further, the spacing control mechanism 204 provides a spatial clearance between the cover unit 101 and the chip 103 with them maintained in parallel relation to each other. In this exemplary embodiment, a pulling unit 503 is provided for implementing the spacing control mechanism 204. The pulling unit 503 pulls the second joint 302 in a direction from the second joint 302 to the fourth joint 304 and thereby pulls the second joint 302 to the end of the cover slide part 501 on the fourth joint side. The range in which the second joint 302 is movable is restricted to the cover slide part 501. Then, an angle 402 between the rotating arm unit 201 and the supporting arm unit 202 is kept at a specified angle.

The rotation control mechanism 205 is connected to the rotating arm unit 201 and the substrate 102. As the rotation control mechanism 205, a torsion spring may be used, for example. The rotation control mechanism 205 controls an angle 401 between the fitting unit and the chip. The angle 401 between the fitting unit and the chip is an angle between an extension of the fitting unit and an extension of the chip as shown in FIG. 1.

The operation of the present device is described hereinbelow.

The operation of the device involves a first operation that makes the cover unit 101 and the chip 103 parallel to each other from the position where the cover unit 101 rotates, and a second operation that makes the connecting member of the fitting unit to fit with the connecting member of the chip with the cover unit 101 and the chip 103 maintained in parallel Positions. Specifically, the first operation changes the state from the state of FIG. 1 to the state of FIG. 2. The second operation changes the state from the state of FIG. 2 to the state of FIG. 3.

First, the first operation is executed. Specifically, the cover unit 101 and the chip 103 are made closer and parallel to each other. A larger force than a force by which the rotation control mechanism 205 rotates the cover unit 101 is applied in a downward direction to the cover unit 101. Then, the rotating arm unit 201 rotates about the first joint 301 as the axis. The cover unit 101, the supporting arm unit 202 and the rotating arm unit 201 operate in conjunction with one another. Therefore, the cover unit 101 and the supporting arm unit 202 also move according the movement of the rotating arm unit 201. At this time, the angle 402 between the rotating arm unit 201 and the supporting arm unit 202 is kept at a specified angle.

When the rotating arm unit 201 rotates, it becomes the state of FIG. 2. The end of the supporting arm unit 202 opposite to the fourth joint 304 when viewed from the third joint 303 (the end of the supporting arm unit) comes into contact with the substrate 102. Therefore, the downward movement of the end of the supporting arm unit 202 is restricted.

The spacing control mechanism 204 makes a certain spacing between the cover unit 101 and the chip 103 (FIG. 2). This is for the purpose of keeping the angle 402 between the rotating arm unit 201 and the supporting arm unit 202 at a specified angle. The certain spacing is a spacing with a width to prevent the fitting unit and the chip to come into contact. When the connecting member of the fitting unit or the connecting member of the chip is a projecting member, the certain spacing preferably has at least a width which prevents the connecting member of the fitting unit and the connecting member of the chip from contacting each other.

Next, the second operation is executed. Specifically, the connecting member 105 of the fitting unit and the connecting member 104 of the chip are made to, fit with each other with the cover unit 101 and the chip 103 maintained in parallel relation to each other.

In order to urge the cover unit 101 against the chip 103 with the cover unit 101 and the chip 103 maintained in parallel relation to each other, the position of the third joint 303 may be adjusted as follows, for example. The center of each of the supporting arm unit 202 and the rotating arm unit 201 is the third joint 303. Each arm unit is joined rotatably to each other about the third joint 303 as the axis. A length from the third joint 303 to the second joint 302 of the rotating arm unit 201 is a length A, and the second joint 302 is positioned in the cover slide part 501. Further, a length from the third joint 303 to the first joint 301 of the rotating arm unit 201 is also the length A. Furthermore, a length from the third joint 303 to the fourth joint 304 of the supporting arm unit 202 is also the length A. A length from the third joint 303 to the end of the supporting arm unit 202 to come into contact with the substrate 102 is also the length A. The members joined by the first joint, the second joint, the third joint and the fourth joint are all rotatable.

When a downward force is applied to the cover unit 101, the end of the supporting arm unit 202 to come into contact with the substrate 102 slides rightward on the substrate 102. Then, the second joint 302 also slides rightward on the cover slide part 501. In this manner, the end of the supporting arm unit 202 and the second joint 302 move in the same direction, which allows the cover unit 101 to move toward the substrate 102, with the cover unit 101 and the substrate 102 remaining in parallel to each other.

Note that a force applied to the cover unit 101 at this time is larger than the sum of a force for the rotation control mechanism 205 to rotate the rotating arm unit 201 and a force for the pulling unit to pull the second joint 302.

By the above-described operation, the cover unit 101 moves toward the substrate 102 with the cover unit 101 and the chip 103 maintained in substantially parallel relation. Then, finally, the connecting member 105 of the cover unit 101 and the connecting member 104 of the chip 103 fit with each other as shown in FIG. 3.

The rotation control mechanism 205 may be mounted outside the immobilizing device. For example, a power source device which includes a power source such as a motor may be prepared separately from the device, and the angle between the fitting unit and the chip may be controlled using the power source device. Further, a user of the device may manually control the angle between the fitting unit and the chip upon usage.

The rotation control mechanism 205 is not limited to the torsion spring. Any element may be used as long as the angle 401 between the fitting unit of the cover unit 101 and the chip 103 can be set larger than zero.

The spacing control mechanism 204 shown in FIG. 1 is just an example, and the spacing control mechanism is not limited thereto. The spacing control mechanism 204 may have any structure as long as it has a mechanism that creates a spatial clearance between the fitting unit and the cover unit 101, in the state where the fitting unit and the cover unit 101 are maintained in parallel relation to each other. The spacing control mechanism 204 may control the spacing between the fitting unit and the chip 103 by controlling the range in which the rotating arm unit 201 and the supporting arm unit 202 rotate about the third joint 303 as the axis. Although a pulling spring is used for the pulling unit as the spacing control mechanism 204, the pulling unit is not limited thereto. The pulling unit may use an elastic body such as rubber, for example, as long as it has a force to pull the second joint 302 toward the fourth joint 304.

The connecting member of the chip 103 and the connecting member of the fitting unit may be in any form as long as the respective connecting members contact and fit with each other. The connecting members may be a socket and a plug, and, for example, the connecting member of the chip may be the socket, and the connecting member of the fitting unit may be the plug.

In this device, the fitting unit and the chip fit with each other with the fitting unit and the chip in parallel to each other. Accordingly, the cover unit and the chip can be crimped together in the state where a pressure is applied equally to both of the cover unit and the chip with use of the device.

Although a slit on the cover unit is provided as the cover slide part in the immobilizing device according to the exemplary embodiment, the form of the cover slide part is not limited thereto. For example, a structure may be employed in which the rotating arm unit slides on the surface of the cover unit and the sliding of the rotating arm unit stops after sliding for a given length. The structure may be implemented by disposing a member for stopping the sliding of the rotating arm unit at one end of the cover slide part, for example.

The substrate 102 of the immobilizing device may have a hollow in its part. As shown in FIG. 1, the hollow is made to make the chip 103 and the cover unit 101 parallel to each other when one end of the supporting arm unit 202 comes into contact with the substrate 102. The hollow is not needed if the chip 103 and the cover unit 101 become parallel to each other.

When one end of the supporting arm unit 202 moves on the substrate 102, one end of the supporting arm unit 202 may slide on the substrate 102 or move in another way. A wheel may be attached to one end of the supporting arm unit 202, and the wheel may be turned on the substrate 102. The same applies to the second joint 302 which slides on the cover slide part.

It is not limited to the substrate 102 on which one end of the supporting arm unit 202 contacts and moves. For example, one end of the supporting arm unit 202 may move on the chip 103.

Although the pulling unit 503 may connect the second joint 302 and the cover unit 101 as shown in FIG. 1, it may connect the rotating arm unit 201 and the cover unit 101. What is necessary for the pulling unit 503 is to pull the second joint 302 toward the third joint 304 and create a spacing between the cover unit 101 and the chip 103.

Although a downward force is applied to the cover unit 101 in the description of the operation of the device in this exemplary embodiment, a component to which a force is applied is not limited thereto. The cover unit 101 operates in conjunction with the rotating arm unit 201 or the supporting arm unit 202. Thus, a force may be applied to the rotating arm unit 201 or the supporting arm unit 202.

Although the cover unit 101 is placed above the substrate 102 in FIG. 1, the positional relationship of the components is not limited thereto. The cover unit 101 may be placed below the substrate 102.

The units may be rotatably joined in any way, as long as each of the joined units can rotate. For example, pin joint may be used.

Figure 22:
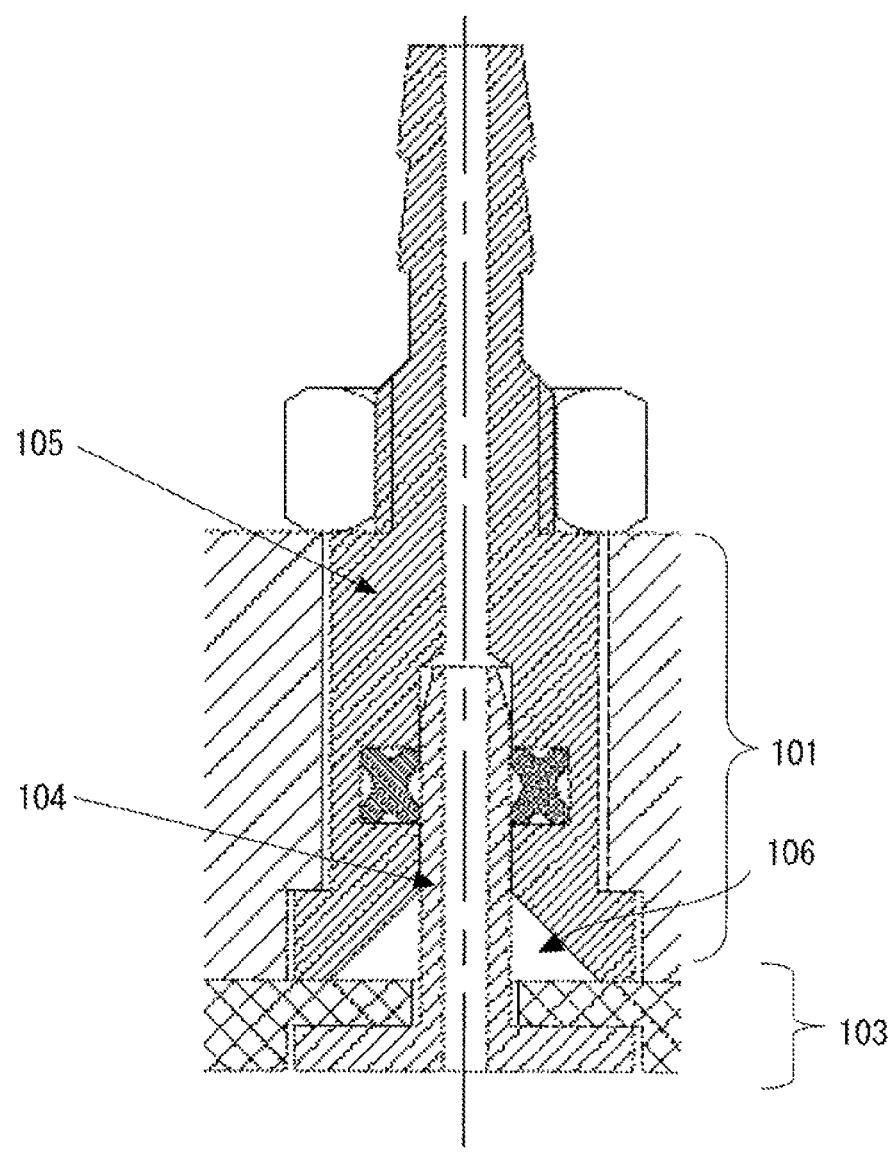
FIG. 22 is a view where an allowance space is provided between a connecting member of a chip and a connecting member of a fitting unit.

The connecting member of the fitting unit and the connecting member of the chip may have a structure that provides an allowance between those components. With the allowance, a failure in alignment of the connecting members, a failure in processing or the like can be compensated. For example, an allowance space 106 is provided in a fitting portion between the connecting member 104 of the chip and the connecting member 105 of the fitting unit as shown in FIG. 22. Then, even if a connection between the connecting member 104 of the chip and the connecting member 105 of the fitting unit is slightly deviated, they can fit with each other in the end.

Further, an allowance may be provided on a fixed surface of the chip which is fixed to the fitting unit or a fixed surface of the fitting unit which is fixed to the chip. By providing an allowance on those fixed surfaces, a failure of fixation between the fitting unit and the chip or the like can be compensated. An example of a method of providing an allowance on the fixed surface of the fitting unit is described below. The cover unit is divided into an arm unit and a fitting unit. The arm unit is joined to the rotating arm unit and the supporting arm unit. The fitting unit has a surface to be fixed to the chip. The fitting unit is joined to the arm unit rotatably about a joint at the center of the arm unit as the axis. Then, a rotation control member is placed so that the rotation of the fitting unit falls within the range from about −5 degrees ($-(\pi/180) \times 5$ rad) to +5 degrees ($+(\pi/180) \times 5$ rad) when the position in which the fitting unit is parallel to the chip is 0 degree. In this structure, an allowance of about 10 degrees ($(\pi/180) \times 10$ rad) with respect to the fixed surface of the chip can be provided on the fixed surface of the fitting unit.

As described above, in the immobilizing device having the structure according to the second exemplary embodiment, it is possible to provide a space for ensuring operability and visibility of the chip 103 between the cover unit 101 and the chip 103 as well as reducing a spatial clearance between the cover unit 101 and the chip 103. Further, it is possible to make the fitting unit and the chip fit with each other with the cover unit 101 and the chip 103 maintained in substantially parallel relation to each other.

Third Exemplary Embodiment

In a third exemplary embodiment, an immobilization device which includes a supporting arm trajectory guide that restricts the movement of the supporting arm unit is described. Note that, because this exemplary embodiment is an application of the first and second exemplary embodiments, explanation of the same points as those of the first and second exemplary embodiments is omitted.

Figure 4:
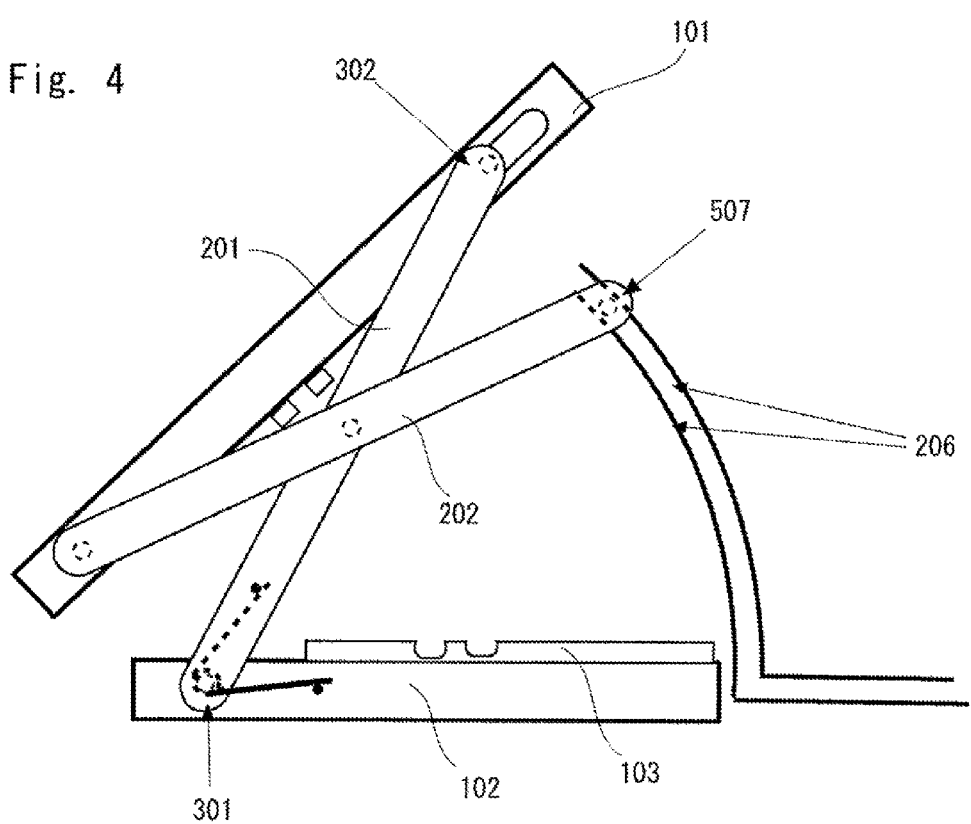
FIG. 4 is a view showing an immobilizing device according to a third exemplary embodiment.

FIG. 4 shows an immobilizing device according to the third exemplary embodiment. The device shown in FIG. 4 includes a supporting arm trajectory guide 206. The supporting arm trajectory guide 206 determines a trajectory along which the supporting arm unit 202 moves. The supporting arm unit 202 is equipped with a supporting arm pin 507. The supporting arm pin 507 is moved along the supporting arm trajectory guide 206. The movement of the supporting arm unit 202 can be thereby restricted.

In this device, when a downward force is applied to the cover unit 101, the supporting arm pin 507 first moves along a circular trajectory. Then, when the supporting arm pin 507 reaches substantially the same height as the substrate 102, the movement of the supporting arm pin 507 along a circular trajectory ends. The cover unit 101 and the chip 103 thereby become parallel to each other.

At this time, the cover unit 101 and the chip 103 are apart at a distance where the connecting member 105 of the fitting unit and the connecting member 104 of the chip do not contact each other.

After that, the supporting arm pin 507 moves rightward along the supporting arm trajectory guide 206. Concurrently, the second joint 302 moves rightward on the cover slide part. According to such an operation, the cover unit 101 moves toward the chip 103, maintained in parallel to the chip 103. Then, the connecting member 105 of the fitting unit and the connecting member 104 of the chip fit with each other.

In this manner, the supporting arm trajectory guide 206 not only controls the trajectory of the movement of the supporting arm unit 202 but also controls the movement of the rotating arm unit 201 and the cover unit 101 which move in conjunction with the supporting arm unit 202. Therefore, both of the spacing control mechanism and the parallel maintaining mechanism can be implemented by the supporting arm trajectory guide 206.

Providing the supporting arm trajectory guide 206 allows reduction of the number of parts of the device. This is because both of the spacing control mechanism and the parallel maintaining mechanism can be implemented by the supporting arm trajectory guide 206. Therefore, the number of parts necessary for the device can be reduced. For example, as shown in FIG. 4, the pulling unit 503 (FIG. 1) is not needed in the device of the third exemplary embodiment.

The material of the supporting arm trajectory guide 206 is not particularly limited as long as it can control the trajectory of the supporting arm unit 202.

The shape and material of the supporting arm pin 507 are not particularly limited as long as it can move the supporting arm unit 202 along the supporting arm trajectory guide 206.

As described above, the immobilizing device which includes the supporting arm trajectory guide 206 is described in the third exemplary embodiment. With inclusion of the supporting arm trajectory guide 206, the number of parts of the immobilizing device can be reduced, thereby enabling simplification and downsizing of the device.

Fourth Exemplary Embodiment

In a fourth exemplary embodiment, an immobilization device which includes a supporting arm trajectory guide that restricts the movement of the supporting arm unit, which is different from that of the third exemplary embodiment, is described. Note that, because this exemplary embodiment is an application of the first or third exemplary embodiment, explanation of the same points as those of the first or third exemplary embodiment is omitted.

Figure 5:
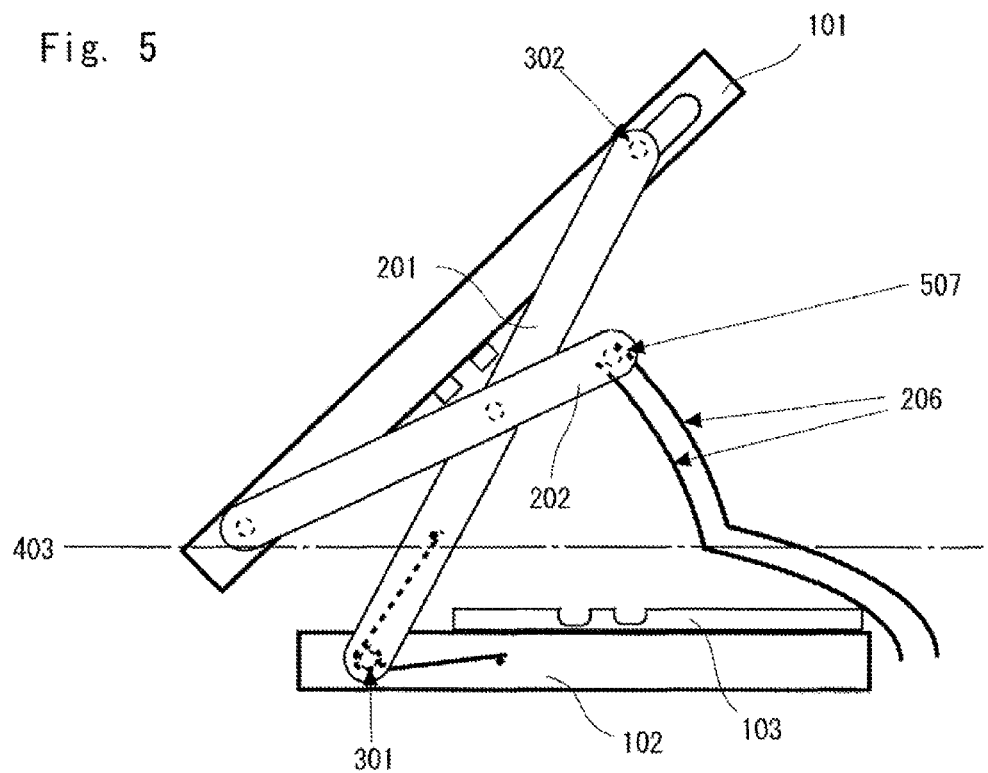
FIG. 5 is a view showing an immobilizing device according to a fourth exemplary embodiment.

FIG. 5 shows an immobilizing device according to the fourth exemplary embodiment. The supporting arm trajectory guide 206 of the device includes a circular trajectory part and an elliptical trajectory part. Further, the length of the supporting arm unit 202 of this device is shorter than the supporting arm unit of the immobilizing device according to the first or third exemplary embodiment. The device shown in FIG. 5 includes the supporting arm trajectory guide 206. The supporting arm trajectory guide 206 determines a trajectory along which the supporting arm unit 202 moves. The supporting arm unit 202 is equipped with the supporting arm pin 507. The supporting arm pin 507 is moved along the supporting arm trajectory guide 206. The movement of the supporting arm unit 202 can be thereby restricted.

In this device, when a downward force is applied to the cover unit 101, the supporting arm pin 507 first moves along the circular trajectory part of the supporting arm trajectory guide 206. Then, when the supporting arm pin 507 reaches the position of a straight line 403, the cover unit 101 and the chip 103 become parallel to each other.

At this time, the cover unit 101 and the chip 103 are apart at a distance where the connecting member 105 of the fitting unit and the connecting member 104 of the chip do not contact each other.

After that, the supporting arm pin 507 moves along the elliptical trajectory part of the supporting arm trajectory guide 206. Concurrently, the cover unit 101 moves toward the substrate 102, maintained in parallel to the substrate 102. Then, the connecting member 105 of the fitting unit and the connecting member 104 of the chip fit with each other.

The supporting arm pin 507 may be the third joint 303. In this case, the supporting arm pin 507 is not necessary to be mounted additionally. The supporting arm pin 507 may be in any form as long as it can control the movement of the supporting arm unit 202 along the trajectory.

As described above, the immobilization device which includes the supporting arm trajectory guide 206 that restricts the movement of the supporting arm unit 202, which is different from that of the third exemplary embodiment, is described in the fourth exemplary embodiment. In this manner, the supporting arm trajectory guide 206 may have various forms, and it may include the circular trajectory part and the elliptical trajectory part, for example.

Fifth Exemplary Embodiment

In a fifth exemplary embodiment, an immobilization device which includes a cover unit trajectory guide that restricts the movement of the cover unit is described. Note that, because this exemplary embodiment is an application of the first to fourth exemplary embodiments, explanation of the same points as those of the first to fourth exemplary embodiments is omitted.

Figure 6:
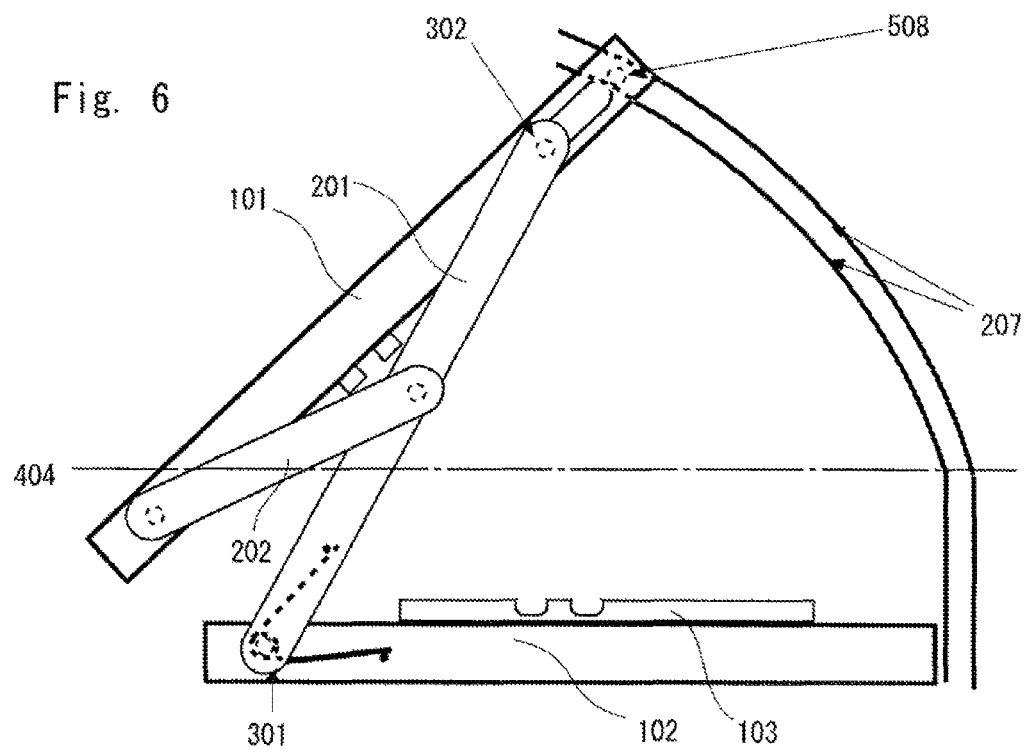
FIG. 6 is a view showing an immobilizing device according to a fifth exemplary embodiment.

FIG. 6 shows an immobilizing device according to the fifth exemplary embodiment. The device shown in FIG. 6 includes a cover unit trajectory guide 207. The cover unit trajectory guide 207 determines a trajectory along which the cover unit 101 moves. The cover unit 101 is equipped with a cover pin 508. The cover pin 508 is moved along the cover unit trajectory guide 207. The movement of the cover unit 101 can be thereby restricted.

In this device, when a downward force is applied to the cover unit 101, the cover pin 508 first moves along a circular trajectory. Then, when the cover pin 508 reaches the position of a straight line 404, the cover unit 101 and the chip 103 become parallel to each other. Then, the trajectory of the cover pin 508 changes from the circular trajectory to a straight trajectory.

At this time, the cover unit 101 and the chip 103 are apart at a distance where the connecting member 105 of the fitting unit and the connecting member 104 of the chip do not contact each other.

After that, the cover pin 508 moves downward along the cover unit trajectory guide 207. Concurrently, the cover unit 101 moves toward the substrate 102, maintained in parallel to the substrate 102. Then, the connecting member 105 of the fitting unit and the connecting member 104 of the chip fit with each other.

In this manner, the cover unit trajectory guide 207 not only controls the trajectory of the movement of the cover unit 101 but also controls the movement of the rotating arm unit 201 and the supporting arm unit 202 which move in conjunction with the cover unit 101. Therefore, both of the spacing control mechanism and the parallel maintaining mechanism can be implemented by the cover unit trajectory guide 207.

Providing the cover unit trajectory guide 207 allows reduction of the number of parts of the device. This is because both of the spacing control mechanism and the parallel maintaining mechanism can be implemented by the cover unit trajectory guide 207. Therefore, the number of parts necessary for the device can be reduced. For example, as shown in FIG. 6, the pulling unit 503 (FIG. 1) is not needed in the device of the fifth exemplary embodiment.

As described above, the immobilizing device which includes the cover unit trajectory guide 207 that restricts the movement of the cover unit 101 is described in the fifth exemplary embodiment. With inclusion of the cover unit trajectory guide 207, the number of parts of the immobilizing device can be reduced, thereby enabling simplification and downsizing of the device.

Sixth Exemplary Embodiment

In a sixth exemplary embodiment, an immobilization device which includes a cover unit trajectory guide that restricts the movement of the cover unit, which is different from that of the fifth exemplary embodiment, is described. Note that, because this exemplary embodiment is an application of the first to fifth exemplary embodiments, explanation of the same points as those of the first to fifth exemplary embodiments is omitted.

Figure 7:
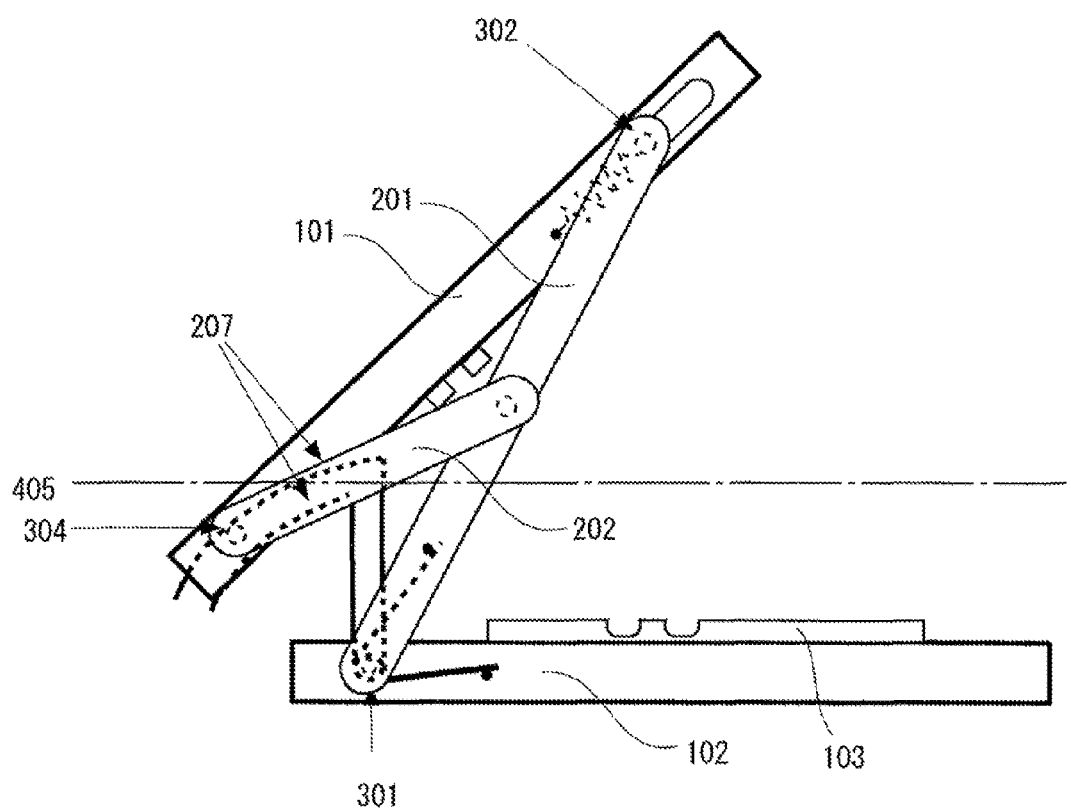
FIG. 7 is a view showing an immobilizing device according to a sixth exemplary embodiment.

FIG. 7 shows an immobilizing device according to the sixth exemplary embodiment. The device shown in FIG. 7 includes a cover unit trajectory guide 207. The cover unit trajectory guide 207 determines a trajectory along which the cover unit 101 moves. The movement of the fourth joint 304 is restricted by the cover unit trajectory guide 207, and the movement of the cover unit 101 is thereby restricted.

In this device, when a downward force is applied to the cover unit 101, the fourth joint 304 first moves along a circular trajectory. Then, when the fourth joint 304 reaches the position of a straight line 405, the cover unit 101 and the chip 103 become parallel to each other. Then, the trajectory of the fourth joint 304 changes from the circular trajectory to a straight trajectory.

At this time, the cover unit 101 and the chip 103 are apart at a distance where the connecting member 105 of the fitting unit and the connecting member 104 of the chip do not contact each other.

After that, the fourth joint 304 moves downward along the cover unit trajectory guide 207. Concurrently, the cover unit 101 moves toward the substrate 102, maintained in parallel to the substrate 102. Then, the connecting member 105 of the fitting unit and the connecting member 104 of the chip fit with each other.

As described above, the immobilization device which includes the cover unit trajectory guide 207 that restricts the movement of the cover unit 101, which is different from that of the fifth exemplary embodiment, is described in the sixth exemplary embodiment. In this manner, the cover unit trajectory guide 207 may have various forms. Further, the fourth joint 304 can be moved along the cover unit trajectory guide 207, so that the movement of the cover unit 101 can be restricted.

Seventh Exemplary Embodiment

In a seventh exemplary embodiment, an immobilization device which includes a chip pressing unit that presses the chip against the substrate is described. Note that, because this exemplary embodiment is an application of the first to sixth exemplary embodiments, explanation of the same points as those of the first to sixth exemplary embodiments is omitted.

Figure 8:
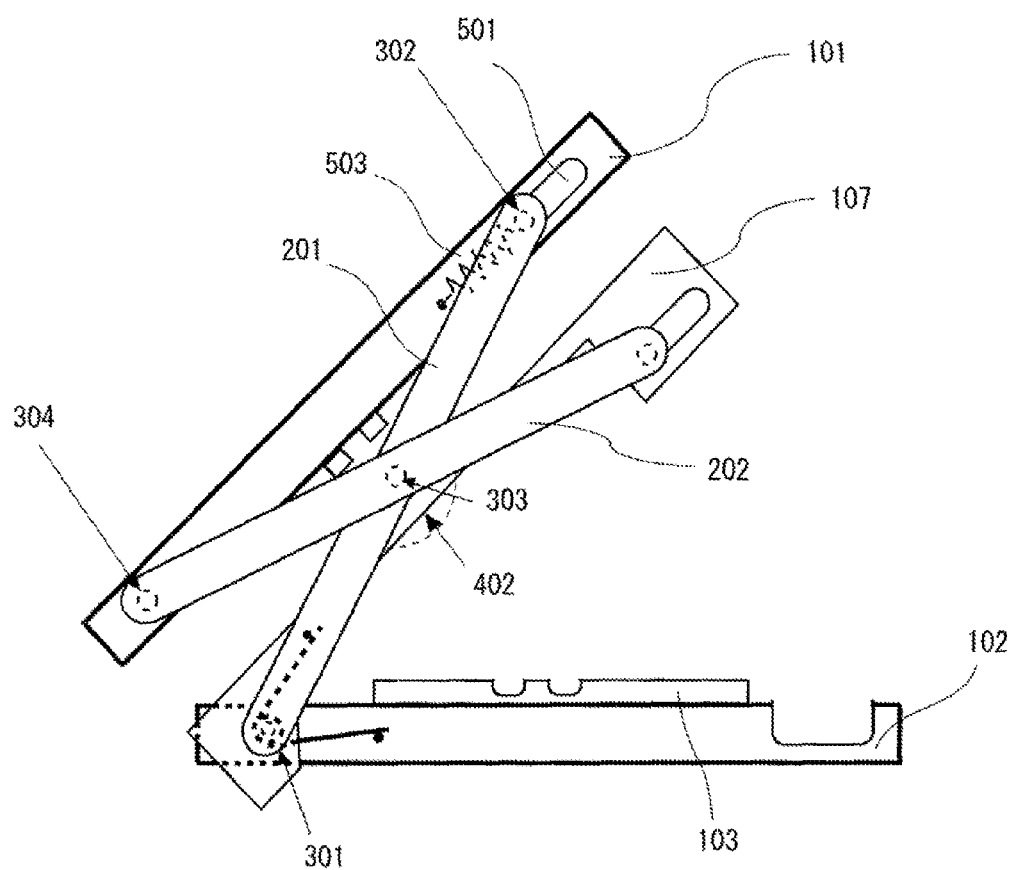
FIG. 8 is a view showing an immobilizing device according to a seventh exemplary embodiment.

FIG. 8 shows an immobilizing device according to the seventh exemplary embodiment. The device shown in FIG. 8 includes a chip pressing unit 107 that presses the chip 103 against the substrate 102. The chip pressing unit 107 presses the chip 103 against the substrate 102 when the cover unit 101 gets closer to the chip 103 in the state of being parallel to the chip 103 (FIG. 9).

Figure 10:
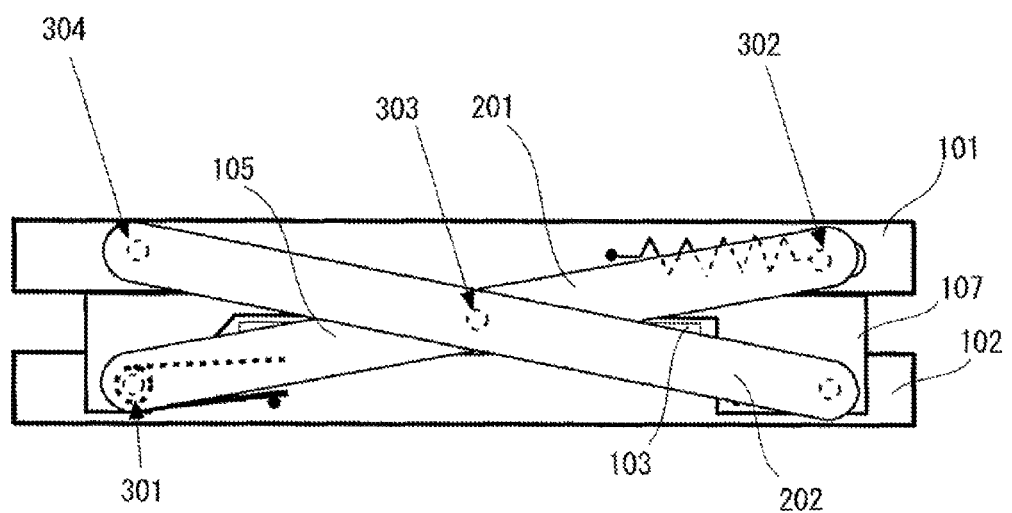
FIG. 10 is a view showing the immobilizing device according to the seventh exemplary embodiment.

Therefore, the connecting member 105 of the fitting unit and the connecting member of the chip 104 can fit together without deviation of the position of the chip 103 on the substrate (FIG. 10).

Figure 9:
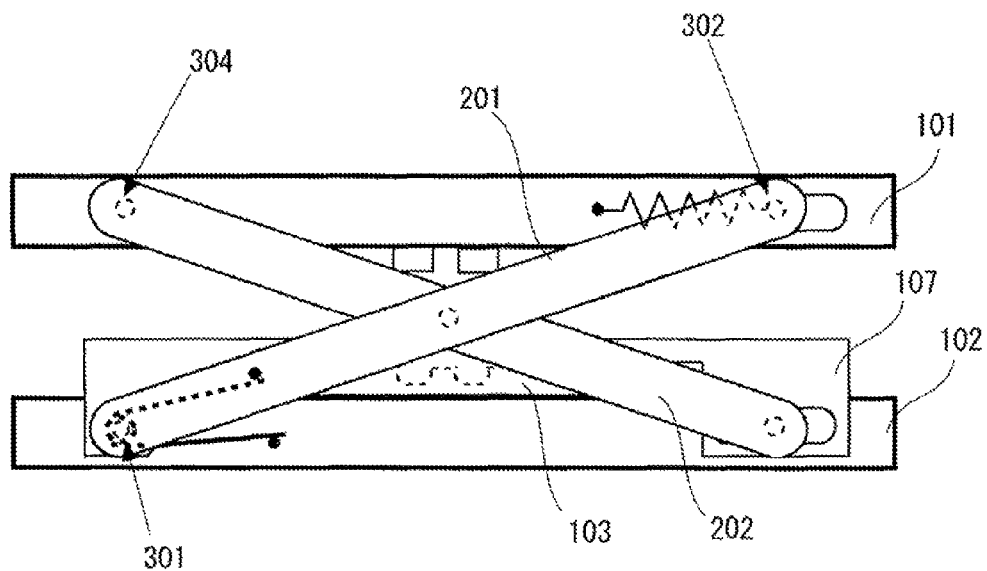
FIG. 9 is a view showing the immobilizing device according to the seventh exemplary embodiment.

Note that the chip pressing unit 107 of FIGS. 8 to 10 is placed on the front side of the fitting unit and the chip, and its part presses the chip down. Therefore, the chip pressing unit 107 does not cover the whole area of the chip.

One end of the chip pressing unit 107 is rotatably joined to the first joint 301. The other end of the chip pressing unit 107 is joined to the supporting arm unit 202. In this structure, the chip pressing unit 107 operates in conjunction with the cover unit 101, the rotating arm unit 201, or the supporting arm unit 202.

The end of the supporting arm unit 202 slides on a part of the chip pressing unit 107. In this structure, a downward force applied to the cover unit 101 is transmitted to the chip pressing unit 107 through the rotating arm unit 201 and the supporting arm unit 202. Because the downward force is applied to the chip pressing unit 107, the chip pressing unit 107 can press the chip 103 down.

The material of a part of the chip pressing unit 107 which is in contact with the chip 103 is preferably an elastic material or the like which can press down the chip 103 placed on the substrate 102 and does not damage the chip 103.

As described above, the immobilization device which includes the chip pressing unit 107 that presses the chip 103 against the substrate 102 is described in the seventh exemplary embodiment. With inclusion of the chip pressing unit 107, deviation of the position of the chip 103 placed on the substrate 102 can be prevented, which enables the connecting member of the fitting unit and the connecting member of the chip to accurately fit with each other.

Eighth Exemplary Embodiment

In an eighth exemplary embodiment, an immobilization device which includes a supporting arm holding unit that can hold an end of the supporting arm unit on the substrate is described. Note that, because this exemplary embodiment is an application of the first to seventh exemplary embodiments, explanation of the same points as those of the first to seventh exemplary embodiments is omitted.

Figure 11:
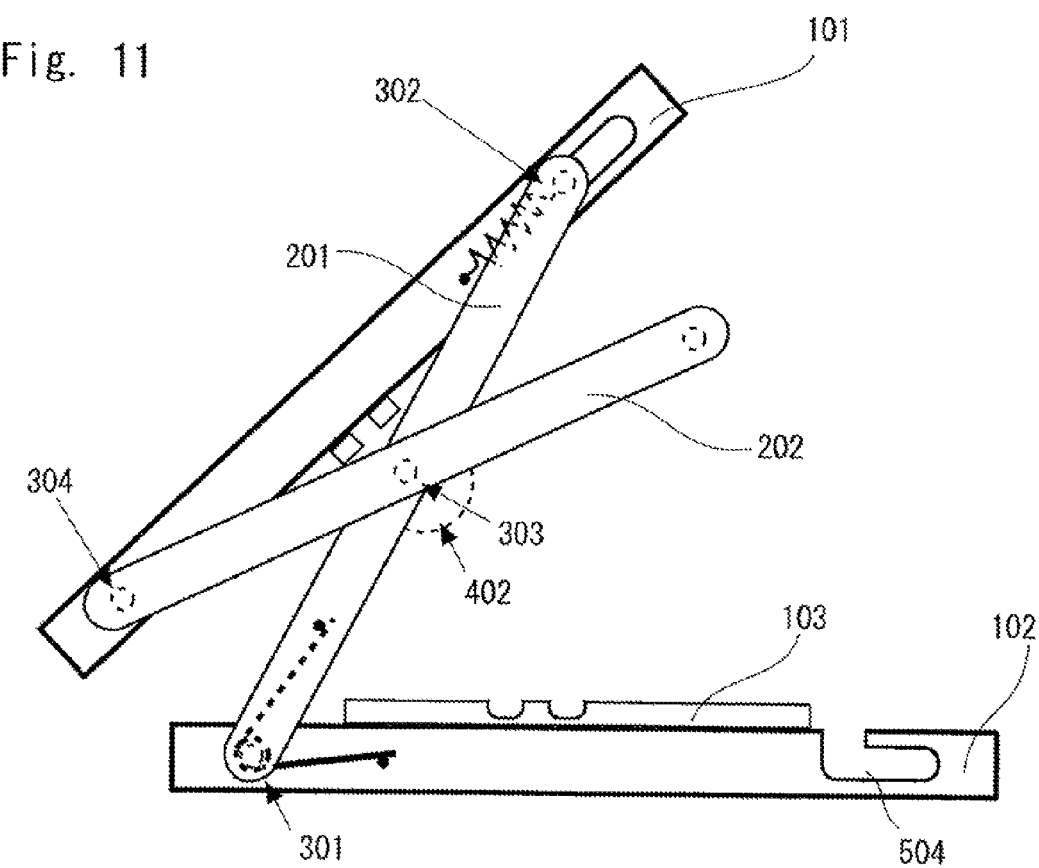
FIG. 11 is a view showing an immobilizing device according to an eighth exemplary embodiment.
Figure 12:
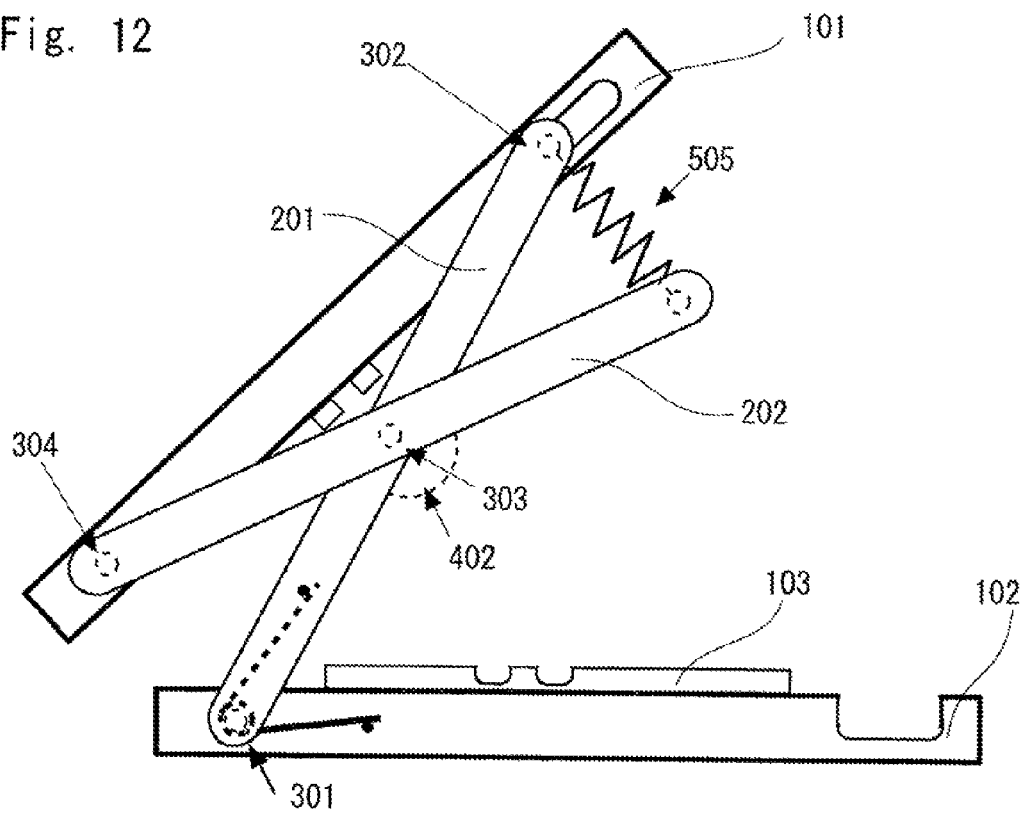
FIG. 12 is a view showing an immobilizing device according to a ninth exemplary embodiment.

FIG. 11 shows an immobilizing device according to the eighth exemplary embodiment. The device shown in FIG. 11 includes a supporting arm holding unit 504 that can hold the end of the supporting arm unit 202 to the substrate 102. By the rotation control mechanism, an upward force is always acting on the supporting arm unit 202 at the position in contact with the substrate 102. However, the upward force acting on the supporting arm unit 202 in contact with the substrate 102 is controlled by the supporting arm holding unit 504. Thus, the end of the supporting arm unit 202 in contact with the substrate 102 does not move in the upward direction and moves only in the cross direction. Thus, when making the connecting member of the fitting unit to fit with the connecting member of the chip, the parallel relation of the cover unit 101 and the chip 103 can be maintained stably.

As described above, the immobilization device which includes the supporting arm holding unit 504 that can hold the end of the supporting arm unit 202 on the substrate 102 is described in the eighth exemplary embodiment. In this immobilization device, the movement of the end of the supporting arm unit 202 is restricted only in the cross direction. Therefore, when making the connecting member of the fitting unit and the connecting member of the chip fit together, the parallel relation of the cover unit 101 and the chip 103 can be maintained in a stable manner.

Ninth Exemplary Embodiment

In a ninth exemplary embodiment, various forms of the spacing control mechanism that provides a certain spacing between the cover unit and the chip are described with reference to FIGS. 12 to 15. Note that, because this exemplary embodiment is an application of the first to eighth exemplary embodiments, explanation of the same points as those of the first to eighth exemplary embodiments is omitted.

In order to provide a certain spacing between the cover unit 101 and the chip 103, a compression spring 505 that connects between the end of the supporting arm unit to come into contact with the substrate 102 and the second joint 302 may be provided. A force of the compression spring 505 acts in the direction of separating the end of the supporting arm unit 202 to come into contact with the substrate 102 and the second joint 302. Therefore, when the end of the supporting arm unit 202 to come into contact with the substrate 102 is in contact with the substrate 102, the angle 402 between the rotating arm unit 201 and the supporting arm unit 202 can be kept to a specified angle. As a result, a certain spacing can be made between the cover unit 101 and the chip 103.

The compression spring 505 may connect between the first joint and the fourth joint.

Figure 13:
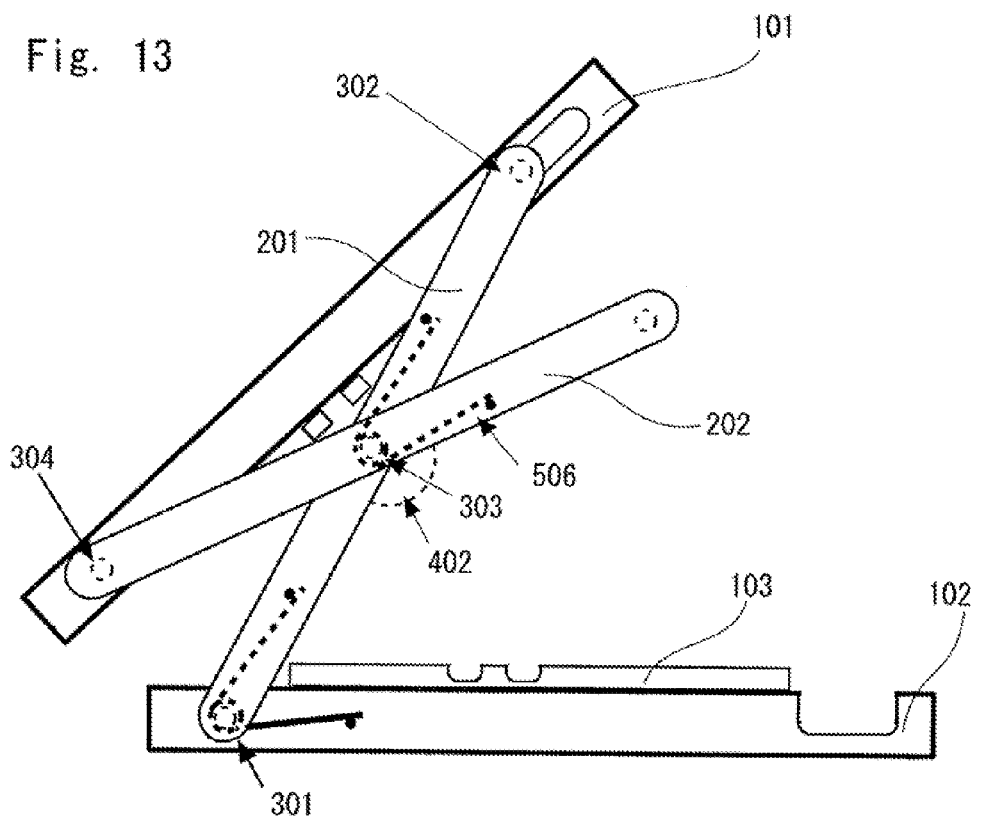
FIG. 13 is a view showing an immobilizing device according to the ninth exemplary embodiment.

Alternatively, a torsion spring 506 may be provided in the third joint 303 as shown in FIG. 13. One end of the torsion spring 506 is connected to the rotating arm unit 201. The other end of the torsion spring 506 is connected to the supporting arm unit 202. In the case of FIG. 13, the torsion spring 506 acts in the direction of separating the end of the supporting arm unit 202 to come into contact with the substrate 102 and the second joint 302. When the end of the supporting arm unit 202 to come into contact with the substrate 102 is in contact with the substrate 102, the angle 402 between the rotating arm unit 201 and the supporting arm unit 202 can be kept to a specified angle. As a result, a certain spacing can be made between the cover unit 101 and the chip 103.

Figure 14:
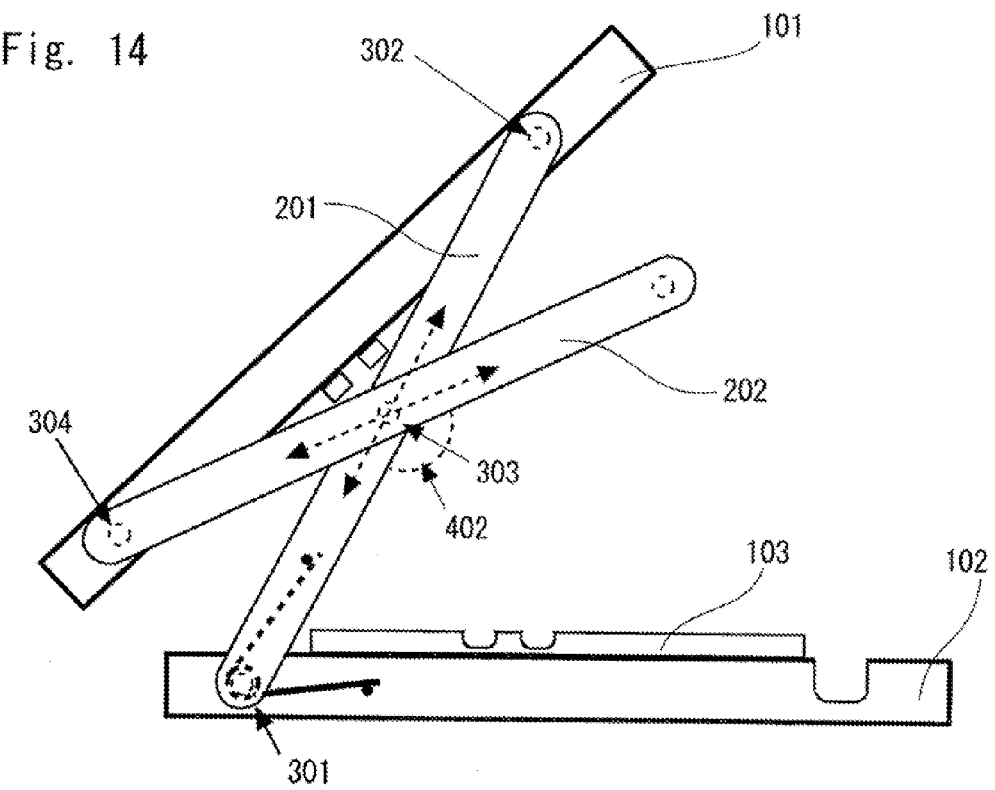
FIG. 14 is a view showing an immobilizing device according to the ninth exemplary embodiment.

Alternatively, the rotating arm unit 201 and the supporting arm unit 202 may equipped with a compression spring mechanism (not shown) as shown in FIG. 14. In the state where a force is not largely applied, the compression spring mechanism expands as illustrated, and thereby the third joint 303 is at a certain spacing from the cover unit 101. As a result, the angle 402 between the rotating arm unit 201 and the supporting arm unit 202 can be kept to a specified angle. Consequently, a certain spacing can be made between the cover unit 101 and the chip 103. When the end of the supporting arm unit 202 is in contact with the substrate 102, and further a force is applied to the cover unit 101, the rotating arm unit 201 and the supporting arm unit 202 are shortened by the compression spring mechanism, and therefore the cover unit 101 and the chip 103 fit with each other.

Figure 15:
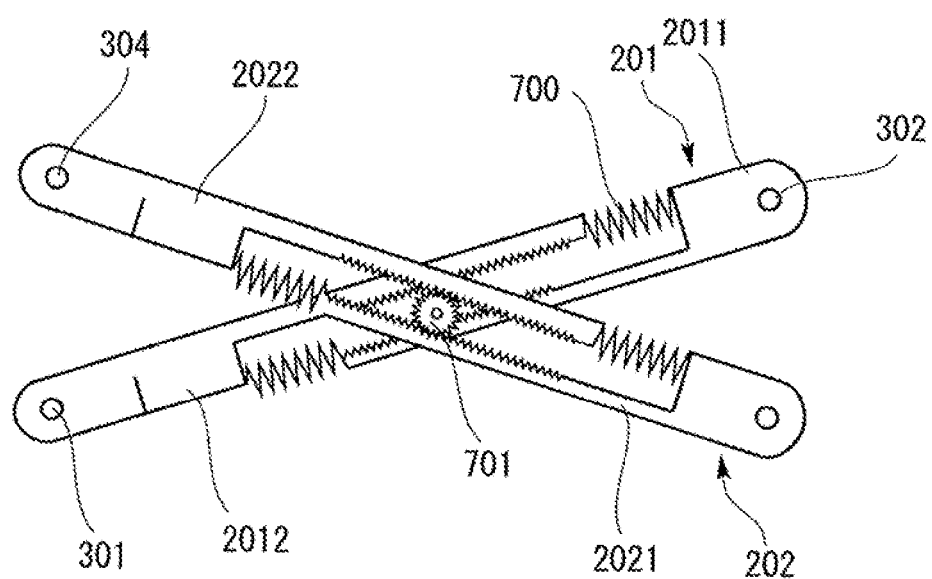
FIG. 15 is a view extracting only a rotating arm unit and a supporting arm unit of an immobilizing device according to the ninth exemplary embodiment.

At this time, the structure as shown in FIG. 15 allows the rotating arm unit 201 and the supporting arm unit 202 to be equally shortened. Specifically, the rotating arm unit 201 includes a first rotating arm piece 2011 and a second rotating arm piece 2012. The first rotating arm piece 2011 and the second rotating arm piece 2012 include gear parts opposed to each other. At an end of the gear part, one of the first rotating arm piece 2011 and the second rotating arm piece 2012 is coupled to the other rotating arm piece through an elastic body 700. A gear wheel 701 is engaged with the opposed gear parts. When the gear wheel 701 rotates in one direction, the first rotating arm piece 2011 and the second rotating arm piece 2012 move closer to each other. On the other hand, when the gear wheel 701 rotates in the other direction, the first rotating arm piece 2011 and the second rotating arm piece 2012 move away from each other.

The supporting arm unit 202 includes a first supporting arm piece 2021 and a second supporting arm piece 2022. The first supporting arm piece 2021 and the second supporting arm piece 2022 include gear parts opposed to each other. At an end of the gear part, one of the first supporting arm piece 2021 and the second supporting arm piece 2022 is coupled to the other rotating arm piece through an elastic body 700. The gear wheel 701, which is common to that of the rotating arm unit 201, is engaged with the opposed gear parts. When the gear wheel 701 rotates in one direction, the first supporting arm piece 2021 and the second supporting arm piece 2022 move closer to each other. On the other hand, when the gear wheel 701 rotates in the other direction, the first supporting arm piece 2021 and the second supporting arm piece 2022 move away from each other. In this manner, each shaft member is moved by the rotation of the common gear wheel 701, so that the rotating arm unit 201 and the supporting arm unit 202 can be equally moved. As a result, the cover unit 101 and the chip 103 can fit with each other, remaining in parallel to each other.

Figure 16:
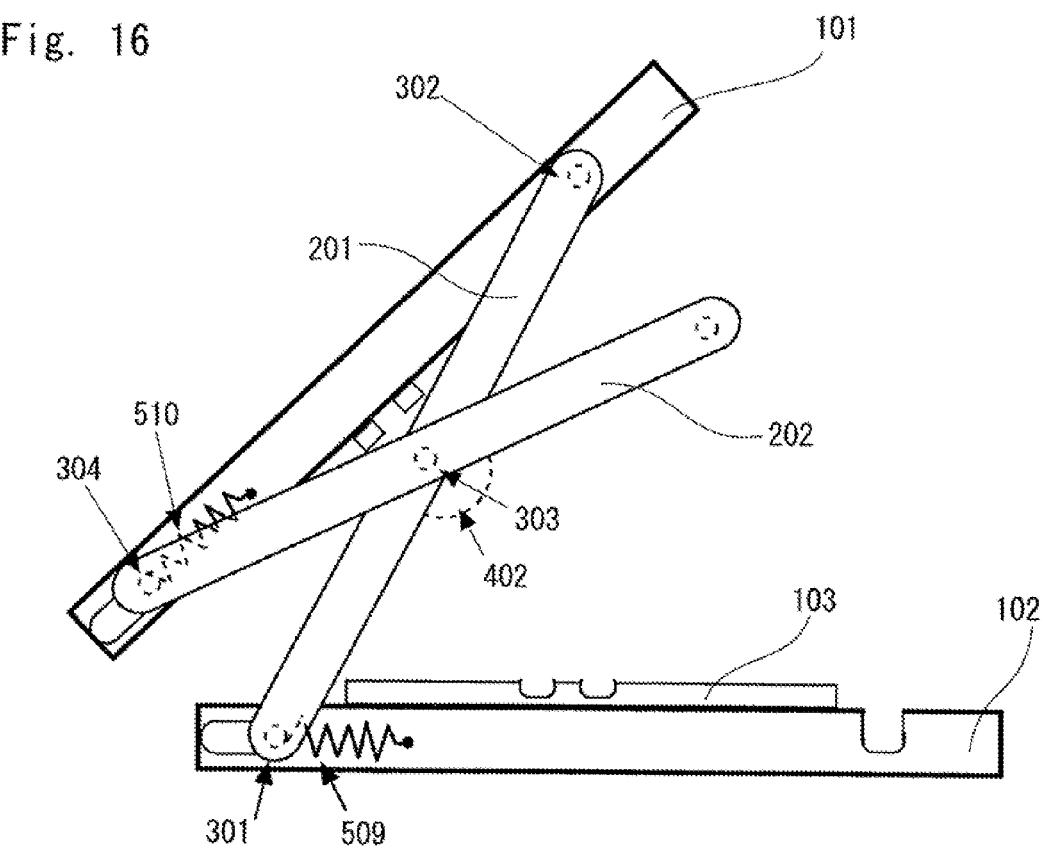
FIG. 16 is a view showing an immobilizing device according to the ninth exemplary embodiment.

Alternatively, a pulling spring 509 may be connected to the first joint 301, and a pulling spring 510 may be connected to the fourth joint 304 as shown in FIG. 16. A slide part which allows sliding is formed on each of the first joint 301 and the fourth joint 304. Thus, when the end of the supporting arm unit 202 to come into contact with the substrate 102 is in contact with the substrate 102, the angle 402 between the rotating arm unit 201 and the supporting arm unit 202 can be kept to a specified angle. As a result, a certain spacing can be made between the cover unit 101 and the chip 103.

As described above, various forms of the spacing control mechanism that provides a certain spacing between the cover unit 101 and the chip 103 are described in the ninth exemplary embodiment. In this manner, the spacing control mechanism may be in various forms, and the spacing control mechanism is not limited to those described in this exemplary embodiment.

Tenth Exemplary Embodiment

In a tenth exemplary embodiment, an immobilization device which includes a tube that is connected to the connecting member of the fitting unit is described. Note that, because this exemplary embodiment is an application of the first to ninth exemplary embodiments, explanation of the same points as those of the first to ninth exemplary embodiments is omitted.

Figure 17:
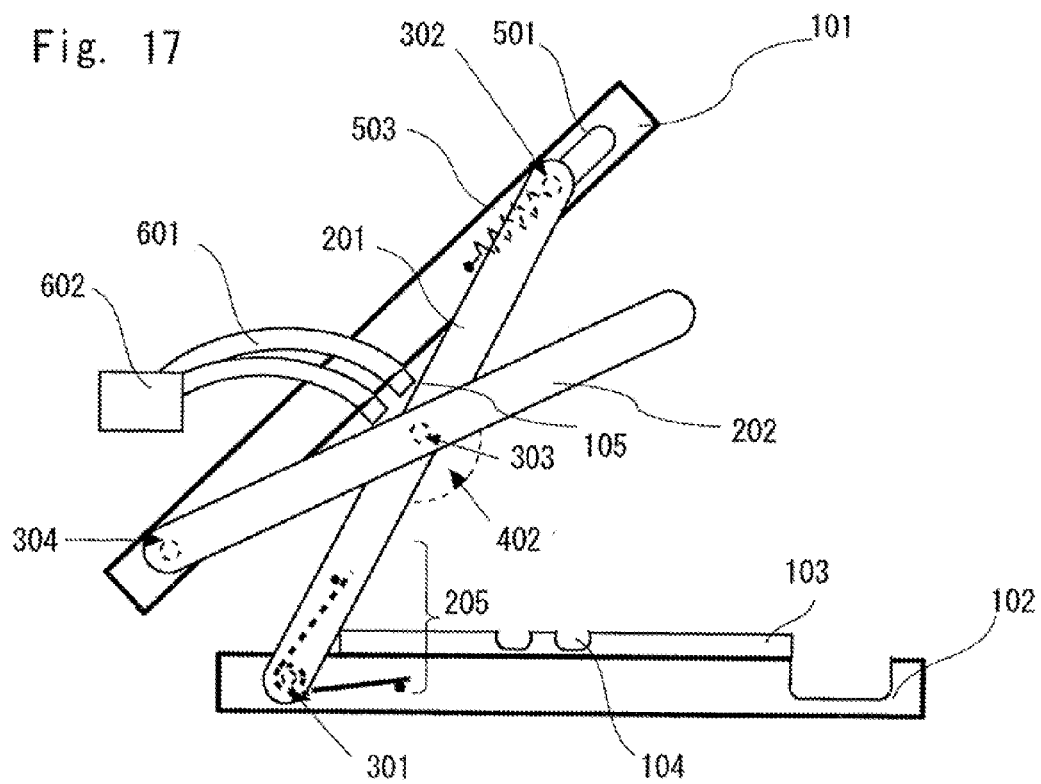
FIG. 17 is a view showing an immobilizing device according to a tenth exemplary embodiment.

FIG. 17 shows an immobilizing device according to the tenth exemplary embodiment. The device shown in FIG. 17 includes a tube 601 which is connected to the connecting member 105 of the fitting unit. One end of the tube 601 is connected to a feeding device 602 that feeds a sample, reagent, pressure or the like. The sample, reagent, pressure or the like fed from the feeding device 602 is fed to the chip 103 through the tube 601 and the connecting member 105 of the fitting unit.

Figure 19A:
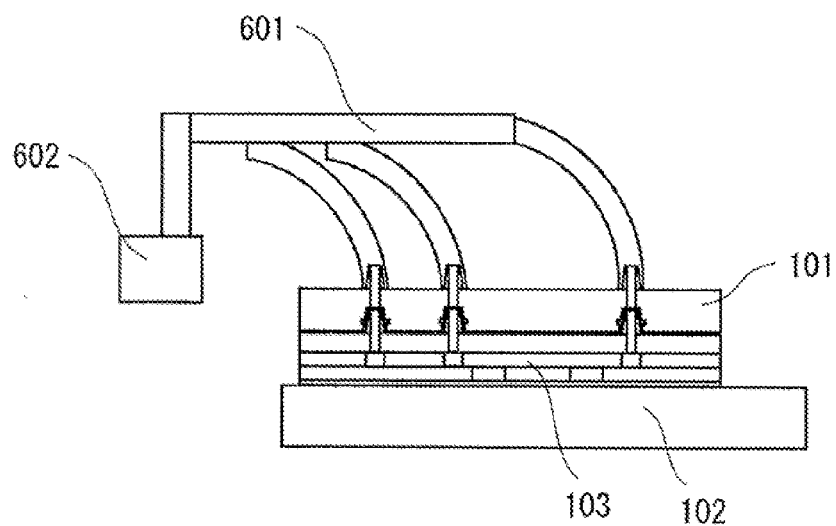
FIG. 19A is a view showing an immobilizing device according to related art.
Figure 19B:
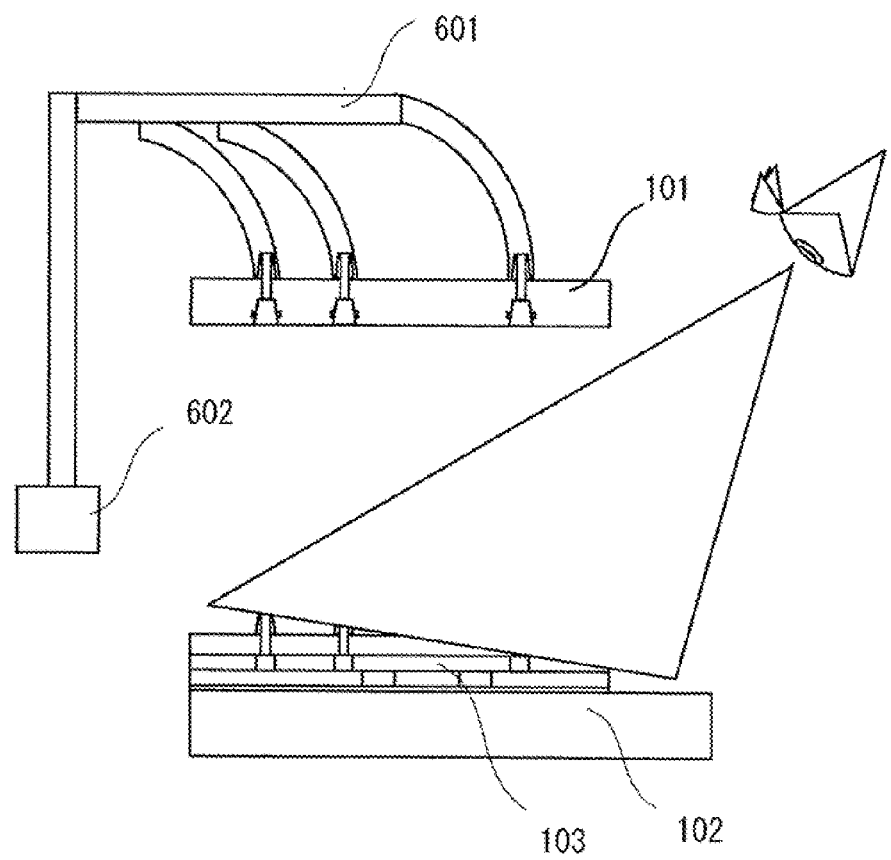
FIG. 19B is a view showing the immobilizing device according to related art.

Use of the immobilizing device according to the present invention allows reduction of the length of the tube 601 to be used. As shown in FIGS. 19A and 19B, in the case of using the device disclosed in Patent Literature 1, a long tube is required when mounting the chip on the substrate. An increase in the length of the tube causes various issues such as complicated handling, difficulty in controlling a pressure inside the tube, and a large dead volume, and thus the long tube is not preferable. In the case of the present device, the moving range of the cover unit which moves at the time of mounting the chip on the substrate is smaller than that of FIG. 19B, and therefore a tube to be used can be short.

The tube may be a generally used one, and its material is not particularly limited.

As described above, the immobilization device which includes the tube connected to the connecting member of the fitting unit is described in the tenth exemplary embodiment. In the immobilization device according to the tenth exemplary embodiment, because the length of the tube 601 can be shortened, advantages such as easier handling of the tube 601, easier pressure control inside the tube 601, and a reduced dead volume are obtained.

Eleventh Exemplary Embodiment

In an eleventh exemplary embodiment, an immobilization device in which the end of the supporting arm unit to come into contact with the substrate is joined to the substrate and which further includes a fitting unit that is rotatably connected to the cover unit is described. Note that, because this exemplary embodiment is an application of the first to tenth exemplary embodiments, explanation of the same points as those of the first to tenth exemplary embodiments is omitted.

Figure 18:
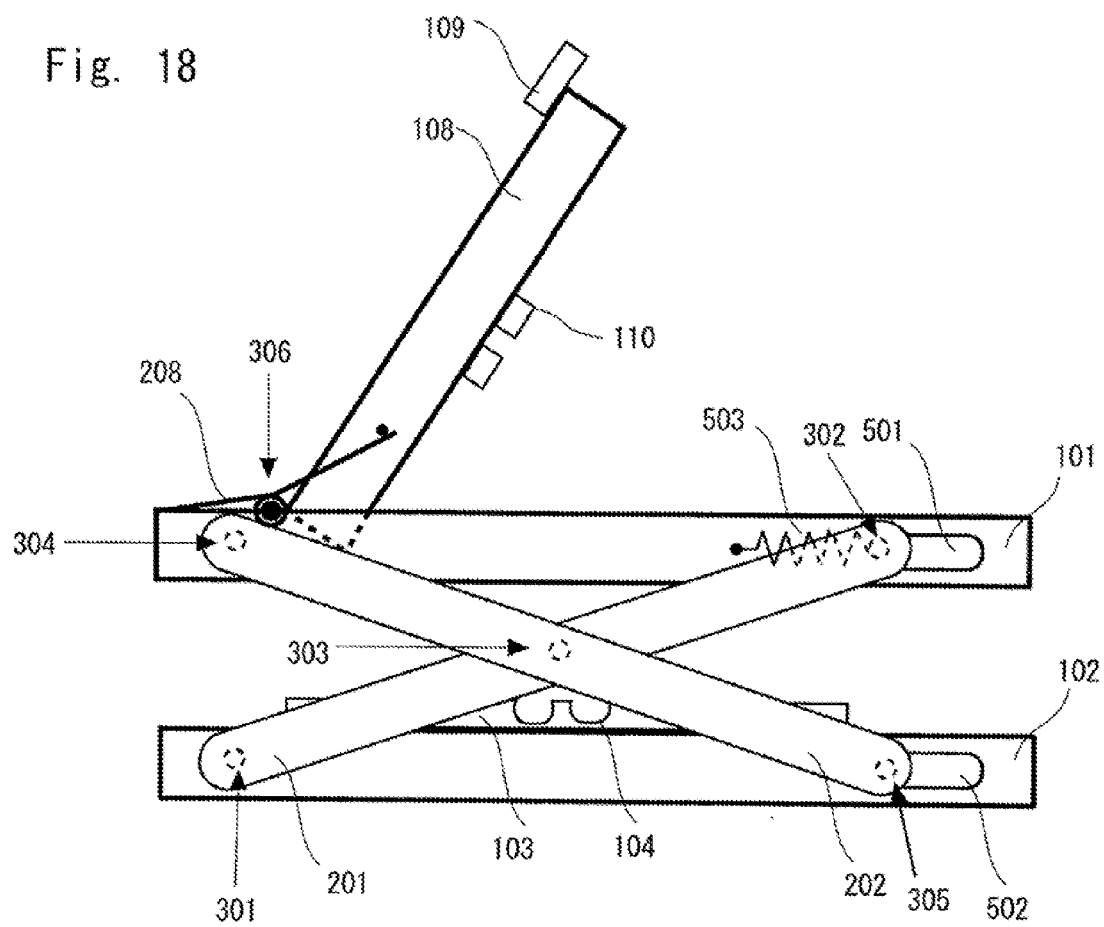
FIG. 18 is a view showing an immobilizing device according to an eleventh exemplary embodiment.

FIG. 18 shows an immobilizing device according to the eleventh exemplary embodiment. In the device shown in FIG. 18, a sixth joint 306 of the cover unit 101 is placed at one end of the cover unit 101. A fitting unit 108 is rotatably connected to the sixth joint 306. The fitting unit 108 has a fitting unit frame 109 that restricts the rotating range of the fitting unit. The fitting unit 108 has a connecting member 110. The connecting member 104 of the chip and the connecting member 110 of the fitting unit fit with each other. In FIG. 18, the cover unit 101 is located on the front of the fitting unit 108, and the fitting unit 108 and the chip 103 are located on the back of the cover unit 101.

Further, the substrate 102 has a substrate slide part 502. One end of the supporting arm unit 202 is joined to a fifth joint 305 of the substrate. The fifth joint 305 is slidable on the substrate slide part 502.

A rotation control mechanism 208 urges the fitting unit 108 to rotate it in the direction of getting away from the cover unit 101.

In this device, the cover unit 101 and the substrate 102 are always in parallel relation to each other. This is because the Scott-Russell mechanism is established by the components of the device as shown in FIG. 18.

The operation of the immobilizing device is described hereinbelow. When a downward force acts on the fitting unit 108, the fitting unit 108 rotates until the fitting unit frame 109 comes into contact with the cover unit 101. The fitting unit frame 109 has the role of stopping the rotation of the fitting unit 108 when the fitting unit 108 becomes parallel to the chip 103 placed on the substrate 102. Thus, when the rotation of the fitting unit 108 stops, the fitting unit 108 and the chip 103 are in parallel, and the cover unit 101 and the fitting unit 108 are combined together.

In this state, a downward force is further applied to the fitting unit 108. When the force becomes larger than the sum of a force for the rotation control mechanism 208 to rotate the fitting unit 108 and a force for the pulling unit 503 to pull the second joint 302, the fitting unit 108 can come closer to the chip 103 in the state where the fitting unit 108 and the cover unit 101 are combined together, with the fitting unit 108 and the chip 103 maintained in parallel relation to each other. Then, the connecting member 110 of the fitting unit and the connecting member 104 of the chip 103 fit with each other.

In this manner, the present invention may have the structure that rotates the fitting unit only. By reducing the number of parts for rotating the fitting unit, a force for rotating the fitting unit can be reduced.

Although the function of the Scott-Russell mechanism is used as one way of implementing the parallel maintaining mechanism in the above description, the parallel maintaining mechanism is not limited thereto. For example, the parallel maintaining mechanism may be implemented by combination of a spur gear and a rack.

The immobilization device in which the end of the supporting arm unit 202 to come into contact with the substrate 102 is joined to the substrate 102 and which further includes the fitting unit 108 that is rotatably connected to the cover unit 101 is described in the eleventh exemplary embodiment. With inclusion of the fitting unit 108 rotatably connected to the cover unit 101, the number of parts of the rotation control mechanism can be reduced. This enables the fitting unit to rotate with a small force.

Although the present invention is described in reference to the exemplary embodiments in the foregoing, the present invention is not limited thereto. Various changes and modifications as would be obvious to one skilled in the art may be made to the structures and details of the present invention within the scope of the present invention.

This application is the National Phase of PCT/JP2009/005459, filed Oct. 19, 2009, which is based upon and claims the benefit of priority from Japanese patent application No. 2008-268905, filed on Oct. 17, 2008, the disclosure of which is incorporated herein in its entirety by reference.

The present invention is applied to the case of performing sample analysis with use of a chip such as μ-TAS.

REFERENCE SIGNS LIST

101 COVER UNIT
102 SUBSTRATE
103 CHIP
104 CONNECTING MEMBER OF CHIP
105 CONNECTING MEMBER OF FITTING UNIT
107 CHIP PRESSING UNIT
108 FITTING UNIT
109 FITTING UNIT FRAME
110 CONNECTING MEMBER OF FITTING UNIT
201 ROTATING ARM UNIT
2011 FIRST ROTATING ARM PIECE
2012 SECOND ROTATING ARM PIECE
202 SUPPORTING ARM UNIT
2021 FIRST SUPPORTING ARM PIECE
2022 SECOND SUPPORTING ARM PIECE
203 PARALLEL MAINTAINING MECHANISM
204 SPACING CONTROL MECHANISM
205 ROTATION CONTROL MECHANISM
206 SUPPORTING ARM TRAJECTORY GUIDE
207 COVER UNIT TRAJECTORY GUIDE
208 ROTATION CONTROL MECHANISM
301 FIRST JOINT
302 SECOND JOINT
303 THIRD JOINT
304 FOURTH JOINT
305 FIFTH JOINT
306 SIXTH JOINT
401 ANGLE BETWEEN FITTING UNIT AND CHIP
402 ANGLE BETWEEN ROTATING ARM UNIT AND SUPPORTING ARM UNIT
501 COVER SLIDE PART
502 SUBSTRATE SLIDE PART
503 PULLING UNIT
504 SUPPORTING ARM HOLDING UNIT
505 COMPRESSION SPRING
506 TORSION SPRING
507 SUPPORTING ARM PIN
508 COVER PIN
509 PULLING SPRING
510 PULLING SPRING
601 TUBE
602 FEEDING DEVICE

The invention claimed is:

1. An immobilization device comprising:
a substrate comprising a first joint and on which a chip having a surface is placed;
a cover unit comprising a second joint and a fitting unit fitting with the chip and rotating freely relative to the chip;
a rotating arm unit rotatably joined to the first joint of the substrate and further joined to the second joint of the cover unit; and
a parallel maintaining mechanism maintaining the fitting unit and the chip parallel to one another, by using the first joint or the second joint, the parallel maintaining mechanism moving along the surface of the chip or along a plane parallel to the surface of the chip.

2. The immobilization device according to claim 1, further comprising:
a spacing control mechanism for controlling a spacing between the fitting unit and the chip.

3. The immobilization device according to claim 1, further comprising:
a rotation control mechanism for controlling an angle between the fitting unit and the chip.

4. The immobilization device according to claim 1, wherein the parallel maintaining mechanism converts a force acting on the fitting unit and perpendicular to the plane parallel to the chip surface into a force parallel to the plane parallel to the chip surface.

5. The immobilization device according to claim 1, wherein the parallel maintaining mechanism is implemented by a Scott-Russell mechanism.

6. The immobilization device according to claim 1, further comprising:
a supporting arm unit rotatably joined to a third joint located between the first joint and the second joint of the rotating arm unit and further joined to a fourth joint of the cover unit.

7. The immobilization device according to claim 1, wherein
the fitting unit is rotatably joined to the cover unit,
a supporting arm unit is comprised rotatably joined to a third joint located between the first joint and the second joint of the rotating arm unit, further joined to a fourth joint of the cover unit, and further joined to a fifth joint of the substrate,
when the first joint moves by the parallel maintaining mechanism, the fourth joint moves along the chip surface or the plane parallel to the chip surface, and
when the second joint moves by the parallel maintaining mechanism, the fifth joint moves along the chip surface or the plane parallel to the chip surface.

8. The immobilization device according to claim 6, wherein the spacing control mechanism controls the spacing between the fitting unit and the chip by controlling a range where the rotating arm unit and the supporting arm unit rotate about the third joint as an axis.

9. The immobilization device according to claim 6, wherein the spacing between the fitting unit and the chip is controlled by an end of the supporting arm unit coming into contact with the substrate or the chip.

10. The immobilization device according to claim 6, wherein
the fitting unit and the chip are in substantially parallel relation when an end of the supporting arm unit comes into contact with the substrate or the chip, and
a direction that the end of the supporting arm unit moves on the substrate or the chip in contact with the substrate or the chip and a direction that the second joint moves along the chip surface or the plane parallel to the chip surface are in the same direction.

11. The immobilization device according to claim 6, comprising:
a chip pressing unit joined to a fifth joint located at an end of the supporting arm unit and further rotatably joined to the first joint.

12. The immobilization device according to claim 6, comprising:
a trajectory restriction guide restricting a trajectory of movement of the supporting arm unit or the cover unit.

13. The immobilization device according to claim 12, wherein the trajectory restriction guide is comprised in the parallel maintaining mechanism.

14. The immobilization device according to claim 12, wherein the trajectory restriction guide is comprised in the spacing control mechanism.

15. The immobilization device according to claim 6, wherein a unit pulling the second joint in a direction from the second joint to the fourth joint is placed in the second joint.

16. The immobilization device according claim 6, wherein a pulling unit pulling the joint in a direction from the fourth joint to the second joint is placed in the joint.

17. The immobilization device according to claim 1, wherein a tube is connected to the fitting unit.

18. The immobilization device according to claim 1, wherein the fitting unit and the chip each have a connecting member.

19. The immobilization device according to claim 18, wherein the spacing control mechanism provides a spacing with at least a width to prevent contact between the connecting member of the cover unit and the connecting member of the chip between the connecting member of the fitting unit and the connecting member of the chip.

\* \* \* \* \*